(12) United States Patent
Nagaoka et al.

(10) Patent No.: US 7,384,602 B2
(45) Date of Patent: Jun. 10, 2008

(54) CHEMICAL ANALYSIS APPARATUS AND GENETIC DIAGNOSTIC APPARATUS

(75) Inventors: Yoshihiro Nagaoka, Ishioka (JP); Naruo Watanabe, Chiyoda (JP); Kei Takenaka, Chiyoda (JP); Tomoki Ohashi, Chiyoda (JP); Yuji Miyahara, Kodaira (JP)

(73) Assignee: Hitachi High-Technologies Corporation, Tokyo (JP)

( * ) Notice: Subject to any disclaimer, the term of this patent is extended or adjusted under 35 U.S.C. 154(b) by 507 days.

(21) Appl. No.: 10/400,445

(22) Filed: Mar. 28, 2003

(65) Prior Publication Data

US 2003/0211010 A1 Nov. 13, 2003

(30) Foreign Application Priority Data

May 8, 2002 (WO) .................. PCT/JP02/04458
Dec. 4, 2002 (JP) ...................... 2002-351901

(51) Int. Cl.
- *C12Q 1/68* (2006.01)
- *G01N 15/06* (2006.01)
- *G01N 33/00* (2006.01)
- *G01N 33/48* (2006.01)
- *G01N 35/00* (2006.01)

(52) U.S. Cl. .................. 422/68.1; 422/50; 422/55; 422/58; 422/81; 422/82; 422/100; 422/101; 422/102; 422/103; 422/104; 436/43; 436/45; 436/63; 436/174; 436/177; 436/180

(58) Field of Classification Search ............... 422/68.1, 422/50, 55, 58, 81, 82, 100–104; 436/43, 436/45, 63, 174, 177, 180

See application file for complete search history.

(56) References Cited

U.S. PATENT DOCUMENTS

| 5,160,702 | A | | 11/1992 | Kopf-Sill et al. |
| 5,173,193 | A | | 12/1992 | Schembri |
| 6,030,581 | A | * | 2/2000 | Virtanen .................... 422/68.1 |

FOREIGN PATENT DOCUMENTS

| EP | 1 459 795 | 9/2004 |
| JP | 2000-514928 | 11/2000 |
| WO | WO 95/01359 A1 | 1/1995 |
| WO | WO 95/33986 | 12/1995 |
| WO | WO 98/13684 A1 | 4/1998 |
| WO | WO 99/3359 A1 | 7/1999 |
| WO | WO 00/78455 A1 | 12/2000 |
| WO | WO 02/097422 | 12/2002 |

* cited by examiner

*Primary Examiner*—Brian Sines
(74) *Attorney, Agent, or Firm*—Antonelli, Terry, Stout & Kraus, LLP.

(57) ABSTRACT

In a chemical analysis apparatus for extracting a specific substance, such as nucleic acid, from a sample containing a plurality of chemical substances, solutions remaining in valves are prevented so that a reagent in an earlier step does not contaminate the subsequent steps. Predetermined quantities of solutions are carried and supplied by centrifugal force without providing valves for controlling the flow of the solutions. After perforating the lids of ventilation holes 272, 273, 274 communicated with a detection container 450 and disposal containers 460 and 470 in an analysis disc 2, the analysis disc 2 is rotated to supply and carry a predetermined quantity of the sample.

2 Claims, 32 Drawing Sheets

FAST ROTATION (SOLUTIONS FLOW)
SLOW ROTATION (POSITIONING)
STOP

CARRIER DISC 12

PERFORATOR 13
DESCEND    ASCEND

POSITION DETECTOR 16

CHEMICAL ANALYSIS APPARATUS AND GENETIC DIAGNOSTIC APPARATUS

BACKGROUND OF THE INVENTION

1. Technical Field

The present invention relates to a chemical analysis apparatus for extracting a specific chemical substance, such as nucleic acid, from a biological sample, such as blood or urine. An extracted chemical substance such as nucleic acid is mixed with a reagent for detection, and the mixture is analyzed. The invention also relates to a genetic diagnostic apparatus equipped with the chemical analysis apparatus.

2. Background Art

As an example of a chemical analysis apparatus for extracting and analyzing a specific chemical substance, such as nucleic acid, from a sample including a plurality of chemical substances, JP Patent Publication (PCT Translation) No. 2001-527220 (WO99/33559) discloses an integrated fluid manipulation cartridge. This device includes a reagent such as a solvent, a washing solution, or an eluent, and a capturing component for capturing nucleic acids. A sample including nucleic acid is injected into the cartridge and mixed with the eluent, and the mixture is passed through the capturing component. Further, the washing solution is passed through the capturing component, and then the eluent is passed through the capturing component. The eluent is brought into contact with a PCR reagent after passing through the capturing component and caused to flow toward a reaction chamber.

As an example of the method of extracting nucleic acids that is employed in the above-mentioned first prior art, JP Patent Publication (PCT Translation) No. 8-501321 (WO95/01359) discloses a method of purifying and separating a nucleic acid mixture by chromatography. In this method, the nucleic acid mixture is adsorbed on a mineral substrate of silica gel, for example, from an aqueous adsorption solution containing a high concentration of salts. The substrate is washed by a washing solution, and nucleic acids are eluted with a solution having a low concentration of salts. The silica gel is fixed inside a hollow cylindrical column, into which a solution of the nucleic acid mixture to be separated is poured and passed through the mineral substrate by suction or centrifugation.

WO00/78455 further discloses a microstructure and a method for examinations based on amplification. The disclosed apparatus, using the nucleic-acid mixture purification and separation method according to the above-mentioned JP Patent Publication (PCT Translation) No. 8-501321 (WO95/01359), passes a DNA mixture through a glass filter as a mineral substrate, and then passes it through a washing solution and an eluent, thereby collecting only DNA. The glass filter is provided on a rotatable structure, and reagents, such as the washing solution and eluent, are stored in individual reagent reservoirs inside the same structure. Each reagent is moved by the centrifugal force created by rotation of the structure, and the reagents are passed through the glass filter by opening a valve provided on a micropath connecting each reagent reservoir and the glass filter.

JP Patent Publication (PCT Application) No. 2001-502793 (WO98/13684) discloses an apparatus and method for chemical analysis. The apparatus comprises a disc-shaped member which has a chamber, paths, a reservoir, and analysis cells. A blood sample is introduced into the centrifugal chamber and centrifuged to separate blood cells from serum. Only the serum is caused to flow into a reaction chamber having beads, the surface of which has been coated with a reagent. Then, a washing solution flows into the reaction chamber, to which an eluting solution further flows. Thereafter, the eluting solution is moved from the reaction chamber to the analysis cells.

In the first prior art, namely that regarding the integrated fluid manipulation cartridge according to JP Patent Publication (PCT Translation) No. 2001-527220 (WO99/33559), when the individual reagents are delivered by pump, the valve or the like provided on the micropath connecting each reagent chamber and the capturing component is opened, thereby passing the reagent through the capturing component. Of the reagents that have passed through the capturing assembly, the washing solution is caused to flow to a waste chamber while the eluent is caused to flow to the reaction chamber by controlling the valve or the like provided on the path between the capturing component and each chamber. When a plurality of reagents are delivered by pump, the reagents remain on the walls of the paths, particularly when there is an obstacle such as a valve. Once such liquids are left, they never move, and it is possible for one reagent to cause contamination at the connecting point. Further, when the washing solution and the elution fluid that have passed through the capturing component are caused to flow to separate chambers by switching the valve or the like, the washing solution that has first flowed to the waste chamber can contaminate the path upstream of the value or the like used for switching to the reaction chamber, possibly resulting in the washing solution mixing with the elution liquid.

According to the second prior art, namely that regarding the purification and separation method disclosed in JP Patent Publication (PCT Translation) No. 8-501321 (WO95/01359), the nucleic acid mixture is introduced into the hollow cylindrical column in which silica gel is fixed. After passing the nucleic acid mixture through the silica gel by centrifugal force, a plurality of reagents are passed through, thereby collecting only nucleic acids. This publication, however, does not disclose the method of introducing the individual reagents into the hollow column or the method of collecting the washing solution and the elution fluid that have been passed through the silica gel.

According to the third prior art, namely that regarding the structure disclosed in WO00/78455, the individual reagents pass through the glass filter when moved by centrifugal force as the valve provided on a micropath connecting each reagent reservoir and the glass filter is opened. While the valve is made of wax that melts when heated, there is a possibility that a reagent that has passed through could remain at the valve and contaminate the collected DNA. Specifically, the DNA mixture or the washing solution may remain in the valve, and it is possible for the remaining DNA mixture or the washing solution to flow into the glass filter as the elution liquid is passed through the glass filter by centrifugal force.

According to the fourth prior art, namely that regarding the apparatus known from JP Patent Publication (PCT Translation) No. 2001-502793 (WO98/13684), when the blood serum is separated, the disc-shaped member revolves around a central axis outside of the disc-shaped member (revolution), and when the serum is guided to the reaction chamber, the disc-shaped member rotates about a central axis within itself (rotation). Thus, individual rotating mechanisms are required for the revolution and the rotation, which complicates the apparatus. Further, when the washing solution and the elution liquid are guided to the reaction chamber, a piston in a cylinder provided inside the disc-shaped member is driven, which further complicates the apparatus.

SUMMARY OF THE INVENTION

It is an object of the invention to solve at least one of the above-described problems and thus provide an inexpensive chemical analysis apparatus for analyzing a specific chemical substance in a liquid sample with high accuracy. Another object of the invention is to provide a genetic diagnostic apparatus comprising the chemical analysis apparatus.

The above objects can be achieved by the invention in which an eluting solution carrier is provided for carrying an eluting solution after a specific chemical substance has been eluted from a captor, and an eluting solution disposal portion is provided in communication with the eluting solution carrier for disposing of part of the eluting solution. In the communication passage communicating the eluting solution carrier with the eluting solution disposal portion, a connecting portion connecting to the eluting solution carrier is located more towards the center of rotation than a connecting portion connecting to the eluting solution disposal portion.

Alternatively, the objects can be achieved by the invention in which an eluting solution carrier for carrying an eluting solution that has passed through the captor has an eluting solution outlet for discharging part of the eluting solution and a disposal opening for disposing of liquids other than the eluting solution, the eluting solution outlet being located more towards the center of rotation than the disposal opening.

Alternatively, the objects can be achieved by the invention comprising:

an eluting solution carrier for carrying an eluting solution after the specific chemical substance has been eluted from the captor;

a waste liquid disposal passage for disposing of liquids other than the eluting solution from the eluting solution carrier; and an eluting solution disposal passage for disposing of part of the eluting solution from the eluting solution carrier, wherein a connecting portion between the eluting solution carrier and the eluting solution disposal passage is located more towards the periphery than an innermost portion of the eluting solution disposal passage.

Alternatively, the objects can be achieved by the invention comprising:

an eluting solution carrier for carrying an eluting solution after the specific chemical substance has been eluted from the captor; and a detection reagent supply passage for supplying a detection reagent to the eluting solution carrier, wherein a connecting portion between the eluting solution carrier and the detection reagent supply passage is located more towards the center of rotation than an innermost portion of the eluting solution disposal passage.

Alternatively, the objects can be achieved by the invention in which carriers are provided individually for a sample solution that has passed through the captor and an eluting solution, wherein a ventilation hole for an eluting solution carrier is opened after the sample solution passed through the captor, so that the eluting solution can pass through the captor.

Alternatively, the objects can be achieved by the invention comprising:

an eluting solution carrier for carrying an eluting solution after the specific chemical substance has been eluted from the captor; and a detection reagent container for supplying a detection reagent to the eluting solution carrier, wherein a detection reagent controller for controlling the flow of the detection reagent is located upstream of a detection reagent outlet for supplying the detection reagent to the eluting solution carrier, and an eluting solution disposal passage for disposing of part of the eluting solution from the eluting solution carrier is provided, wherein the detection reagent is caused to flow to the eluting solution carrier after part of the eluting solution has been disposed from the eluting solution disposal passage.

Particularly, the reagent controller may comprise an openable ventilation hole and a hole-opening mechanism.

The reagent controller may be a reagent dispenser.

The objects can be achieved by the invention comprising:

an eluting solution carrier for carrying an eluting solution that has passed through the captor; and a flow passage for the flow of the solution from the eluting solution carrier, wherein a flow passage entrance connecting the eluting solution carrier and the flow passage is located more towards the center of rotation than a flow passage exit on another end of the flow passage, wherein after the reagent that has passed through the captor during the rotation of the rotary structural member flowed through the flow passage, the rotary structural member is stopped, rotated again, and then stopped again, and thereafter the eluting solution is caused to pass through the captor.

The objects can be achieved by the invention in which liquid that remains after a predetermined quantity of sample is separated from the sample dispensed into the structural member is caused to flow down to one of the reagent containers.

Alternatively, the objects can be achieved by a chemical analysis apparatus comprising a flow passage for separating a predetermined quantity of a sample dispensed into a rotary structural member by centrifugation, wherein remaining sample liquid is caused to flow down to one of reagent containers.

Further, the objects can be achieved by a genetic diagnostic apparatus comprising the above chemical analysis apparatus.

DESCRIPTION OF THE INVENTION

Embodiment 1

An embodiment of the chemical analysis apparatus according to the invention will be described by referring to FIGS. 1 to 17.

Figure 1:
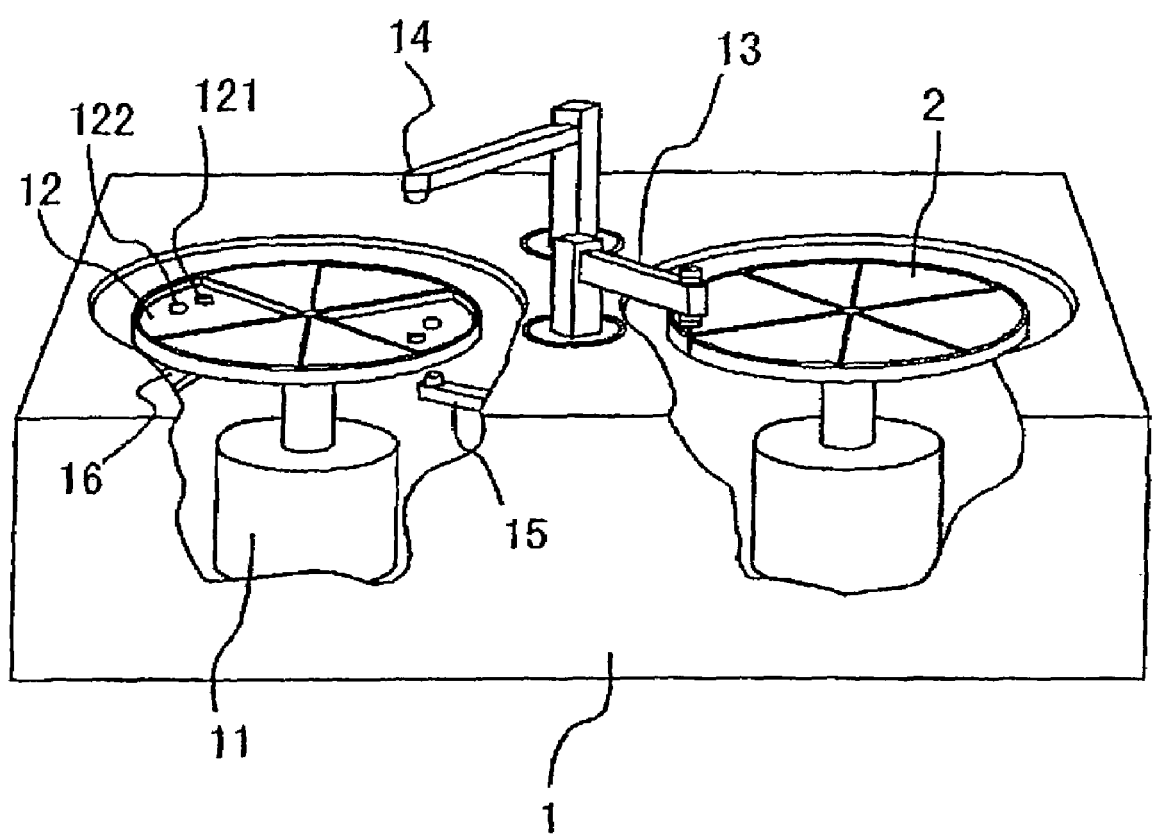
FIG. 1 shows the overall structure of a genetic analysis apparatus according to the invention.

FIG. 1 is an overall view of a genetic analysis apparatus 1 according to the invention. The genetic analysis apparatus 1 includes a carrier disc 12 rotatably supported by a motor 11, a plurality of sectored analysis discs 2 positioned via a protrusion 121 on the carrier disc 12, a perforator 13 for controlling the flow of solutions, two optical devices for heating and detection, namely an upper optical device 14 and a lower optical device 15, and a positioning sensor 16, which will be described later (FIG. 18). The carrier disc 12 includes a carrier disc optical window 122 for the lower optical device 15.

Figure 2:
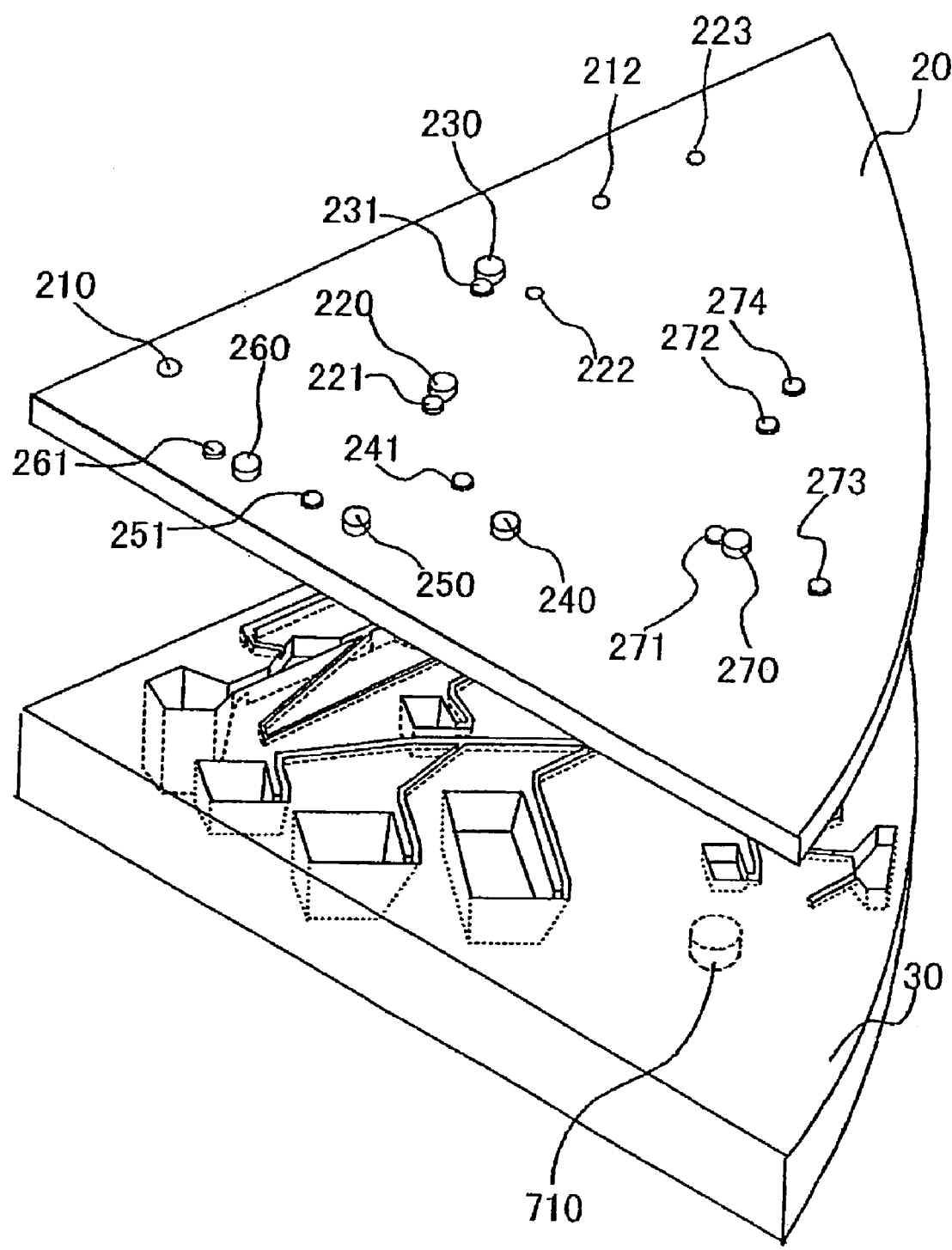
FIG. 2 shows the structure of an analysis disc according to the invention

FIG. 2 shows the structure of the analysis disc 2, which comprises an upper cover 20 and a fluid passage portion 30 joined together. The upper cover 20 includes a sample inlet 210, a plurality of reagent inlets 220, 230, 240, 250, 260, and 270, a plurality of ventilation holes 212, 222, and 223, and a plurality of lidded ventilation holes 221, 231, 241, 251, 261, 271 272, 273, and 274. The flow passage portion 30 includes a positioning hole 710, containers to be described later, and passages. The analysis disc 2 is positioned when the positioning hole 710 fits with the protrusion 121 of the carrier disc 12.

Figure 3:
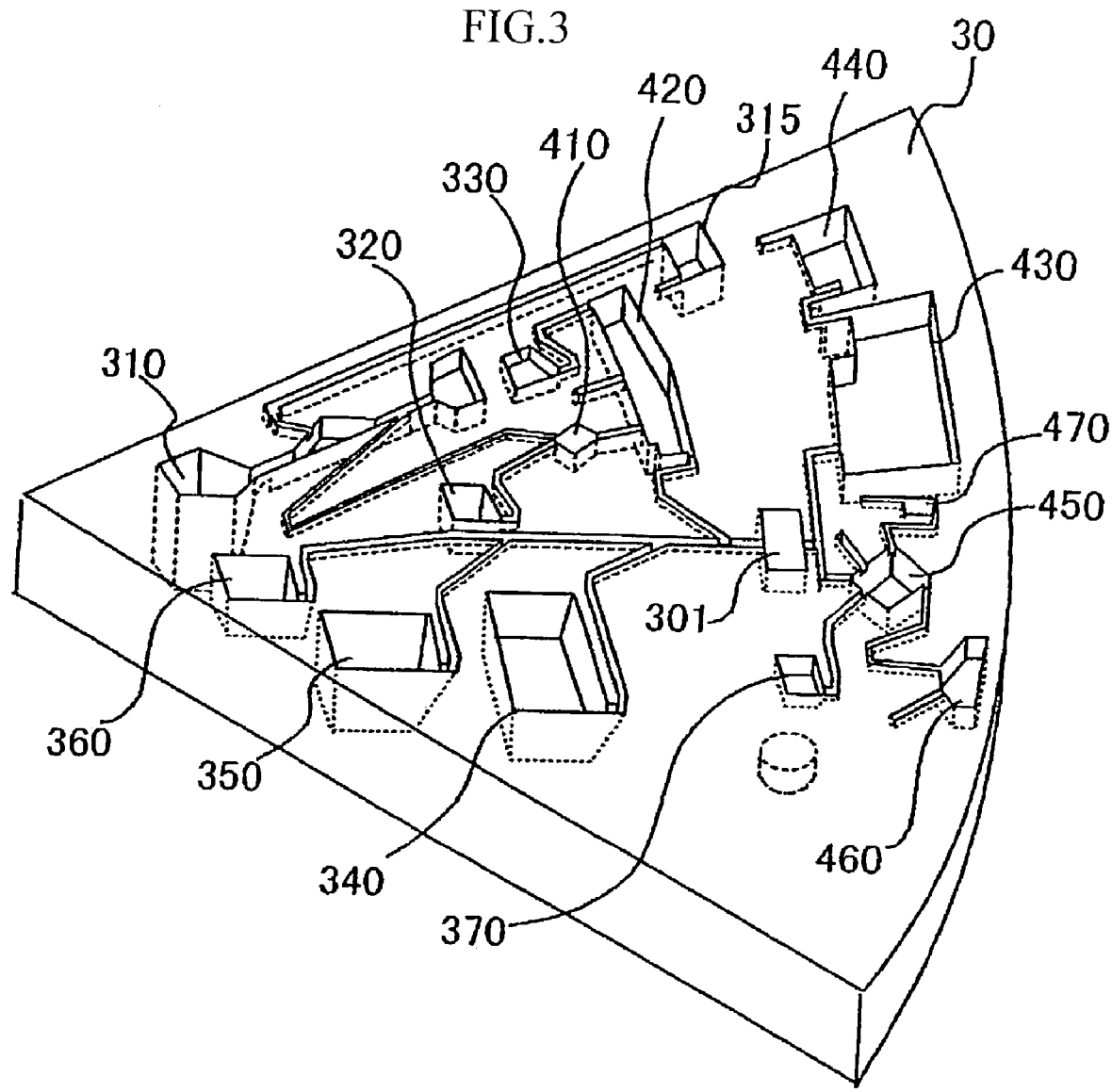
FIG. 3 shows the structure of a flow passage portion according to the invention.

FIG. 3 shows an example of the fluid passage portion 30, which comprises passages that are used when blood serum is separated from whole blood, nucleic acids contained in a virus in the blood serum are extracted, a solution of the extracted nucleic acids is quantitatively determined, and a detection reagent is added to analyze the solution.

Figure 4:
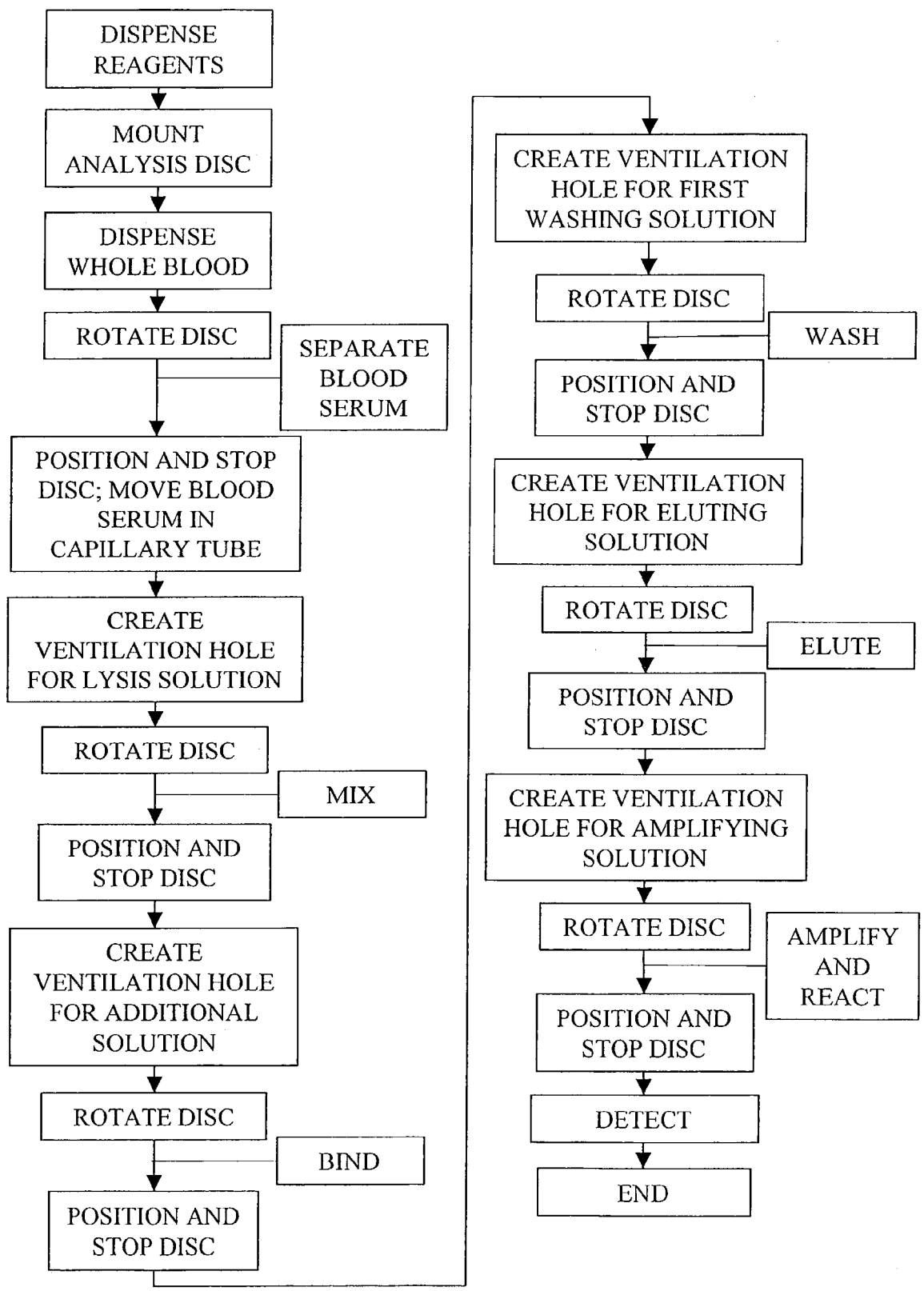
FIG. 4 shows the flow of analysis operation according to the invention.
Figure 5:
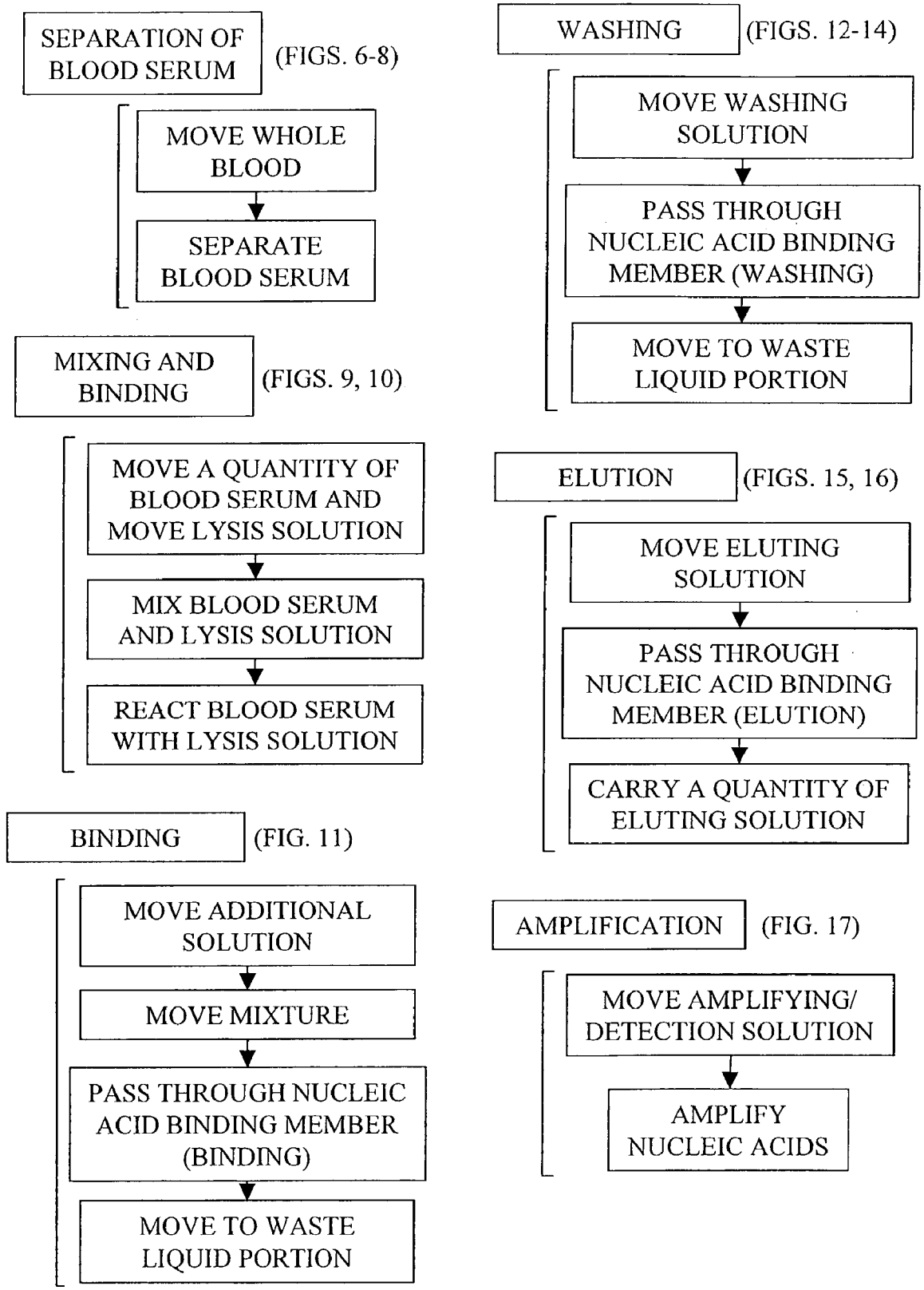
FIG. 5 shows the individual operations during analysis and illustrates their correspondence to the individual figures.

Hereafter, the operation for extraction and analysis of viral nucleic acids will be described for a case where whole blood is used as the sample. The flow of the extraction and analysis is depicted in FIGS. 4 and 5. The fluid states in the flow passage portion 30 will be described step by step by referring to FIGS. 6 to 17.

An operator dispenses a reagent via each of the reagent inlets 220, 230, 240, 250, 260, and 270 on the upper cover 20 of the analysis disc 2 into each of reagent containers 320, 330, 340, 350, 360, and 370, and closes their lids. Depending on the number of analyses, the reagents are injected into as many analysis discs as necessary. The analysis discs are then mounted on the carrier disc 12.

Figure 6:
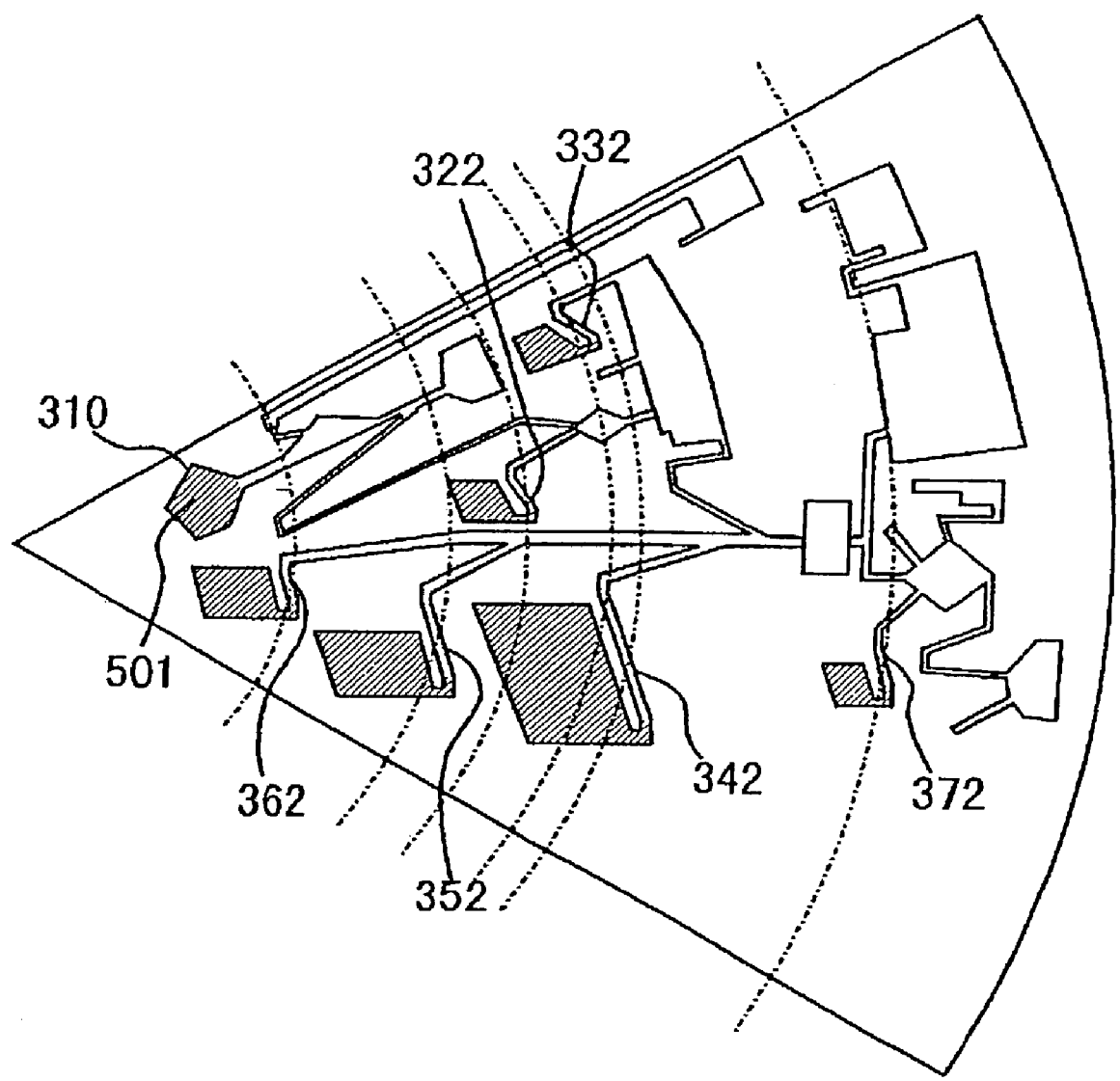
FIG. 6 illustrates the operation of the flow passage portion during separation of blood serum according to the invention.

Then, whole blood collected by a vacuum blood-collecting tube, for example, is introduced via the sample inlet 210 into the sample container 310 (FIG. 6).

Figure 7:
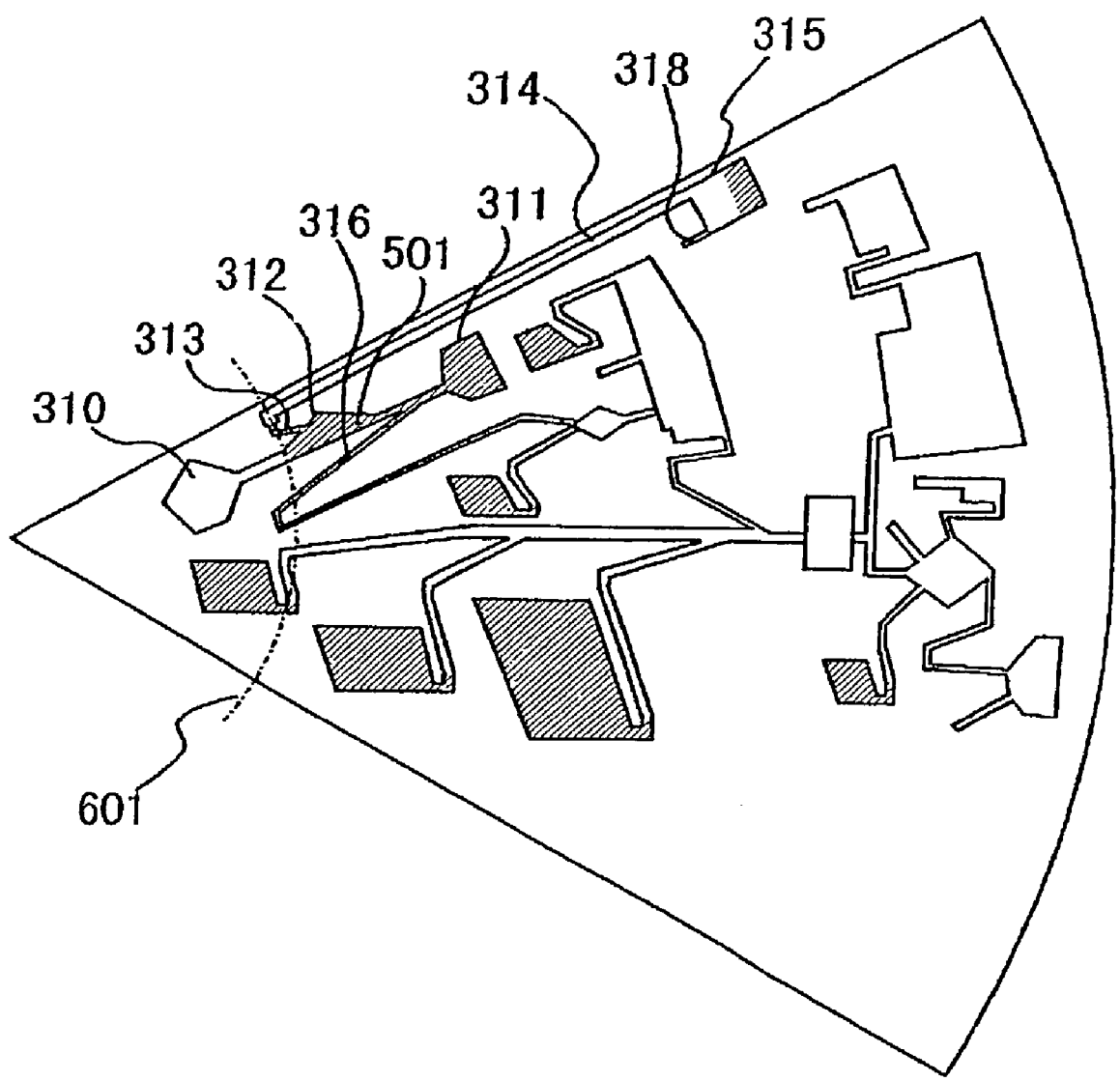
FIG. 7 illustrates the operation of the flow passage portion during separation of blood serum according to the invention.

After the whole blood 501 is introduced, the carrier disc 12 is rotated by the motor 11. The whole blood introduced into the sample container 310 moves towards the periphery on account of the centrifugal force created as the carrier disc 12 is rotated. The whole blood thus fills a blood cell storage container 311 and a blood serum quantitative determination container 312, and excess whole blood flows via an narrow overflow passage 313 and an wide overflow passage 314 into a whole-blood disposal container 315 (FIG. 7). The whole-blood disposal container 315 has a ventilation passage 318 for disposing of whole blood. Further, there is a ventilation hole 212 for disposing of whole blood in the upper cover 20 at a position corresponding to an innermost portion of the whole-blood disposing ventilation passage 318, allowing free passage of air. The connecting portion between the narrow overflow passage 313 and the wide overflow passage 314 increases in size suddenly and is located at the innermost side of the thin overflow passage 313 (radius position 601). Thus, the whole blood just fills the thin overflow passage 313 and does not flow beyond the connecting portion. Accordingly, because no liquid can exist beyond the radius position 601 towards the center of the disc, the liquid level of the blood serum determination container 312 is also flush with the radius position 601. The whole blood also flows into a blood serum capillary tube 316 branching off from the blood serum quantitative determination container 312, where the innermost portion of the whole blood is also located at the radius position 601.

Figure 8:
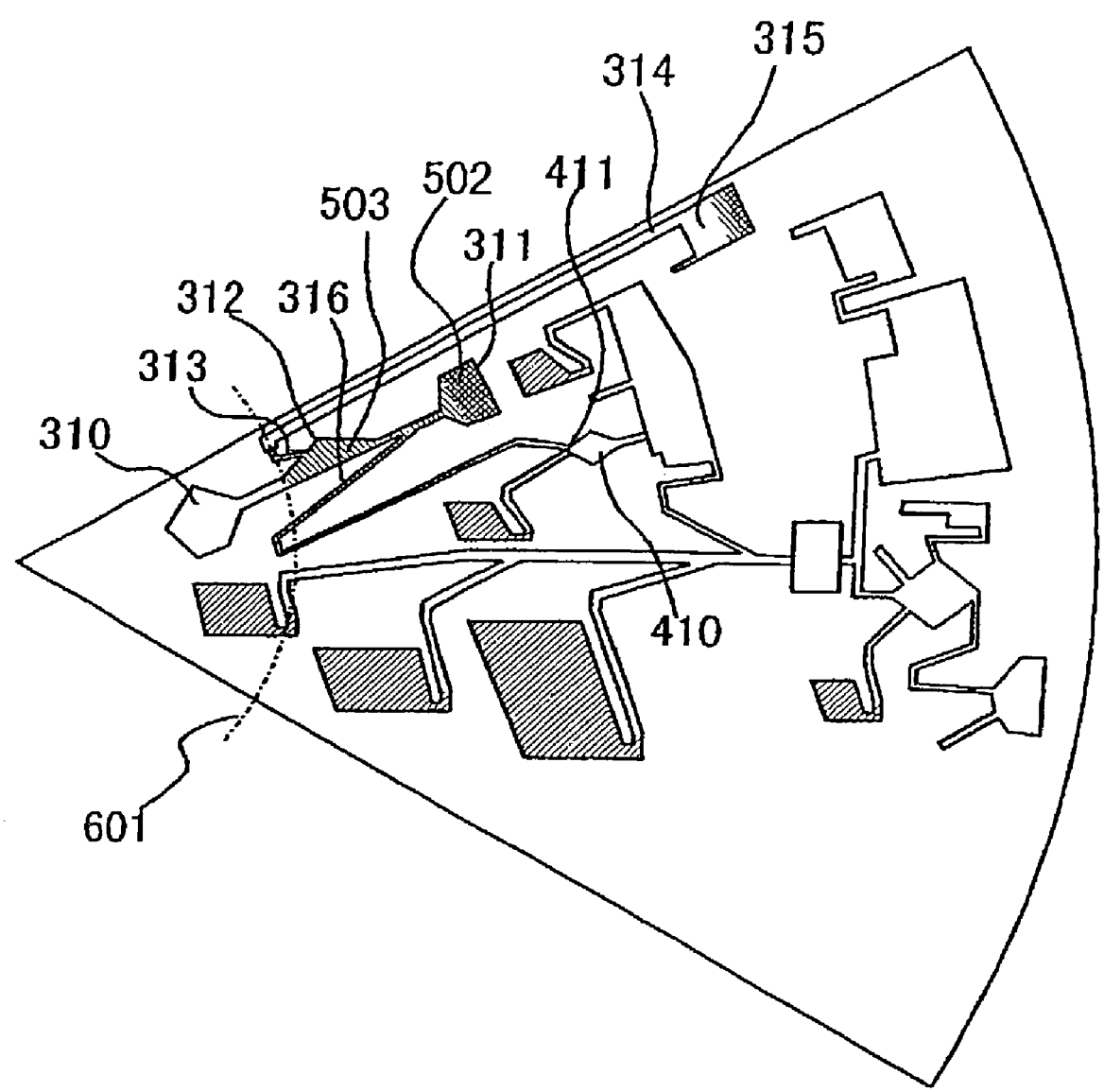
FIG. 8 illustrates the operation of the flow passage portion during separation of blood serum according to the invention.

As the rotation is further continued, the whole blood 501 is separated into blood cells and blood serum (centrifugal separation). As a result, the blood cells 502 are moved to the blood-cell storage container 311 on the peripheral side, so that the blood-serum quantitative determination container is filled only with the blood serum 503 (FIG. 8).

During the above-described sequence of blood serum separation operation, the ventilation holes 221, 231, 241, 251, 261, and 271 in the upper cover 20 for each reagent container are closed by the lids, and thus are airtight. Although the individual reagents tend to flow out via the peripheral side of the reagent containers due to centrifugal force, the airtightness of the containers lowers the pressure inside them, which balances the centrifugal force and prevents the reagents from escaping. However, as the rotation speed increases and the centrifugal force becomes greater, the pressure inside each reagent container gradually decreases further, and once the pressure drops below the saturation vapor pressure of the reagent, bubbles are formed. Accordingly, a flow passage structure (backward passages 322, 332, 342, 352, 362, and 372) is adopted, as shown in FIG. 6, whereby the reagent flowing out of each reagent container from the peripheral side can be brought back towards the center of rotation, thus controlling the pressure reduction in the reagent containers and preventing the generation of bubbles. This way, the individual reagents are held inside the reagent containers and do not flow during the blood-serum separating operation.

After the analysis disc is rotated for a predetermined period of time and the blood serum separating operation is finished, the analysis disc 2 comes to a stop. Part of the blood serum 503 in the blood-serum quantitative determination container 312 moves into the capillary tube 316 due to capillary phenomena by surface tension up to a mixing portion entrance 411, where the mixing portion 410 and the blood-serum capillary tube 316 are connected. Thus, the blood-serum capillary tube 316 is filled with the blood serum.

Figure 18A:
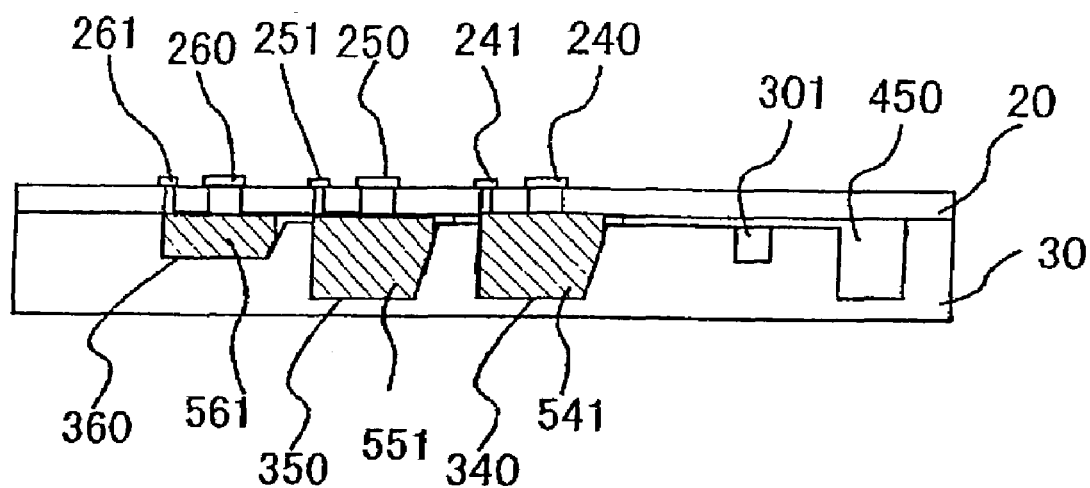
FIGS. 18(a) and 18(b) are cross-sectional views of the reagent inlets and ventilation holes of each reagent container according to the invention.
Figure 18B:
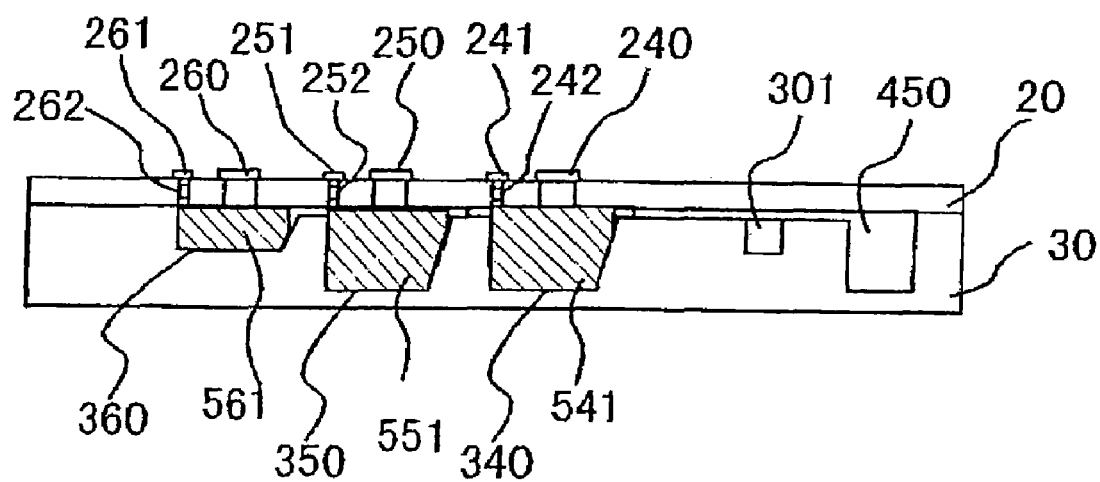

Thereafter the motor 11 is rotated as the perforator 13 perforates the lid of the ventilation hole above each of the reagent containers one by one, thus moving the individual reagents by centrifugal force. As shown in the cross-sectional view of the analysis disc in FIG. 18(a), the upper cover 20 has reagent inlets (240, 250, 260) and ventilation holes (241, 251, 261) above the individual reagent containers, and each ventilation hole is covered by a lid. By perforating the lid with the perforator 13, air is allowed to enter into the reagent container. Further, as shown in FIG. 18(b), filters 242, 252, and 262 are provided between the ventilation holes and the reagent containers in order to prevent contamination of the perforator 13.

Hereafter, the operation after the completion of blood serum separation will be described.

Figure 9:
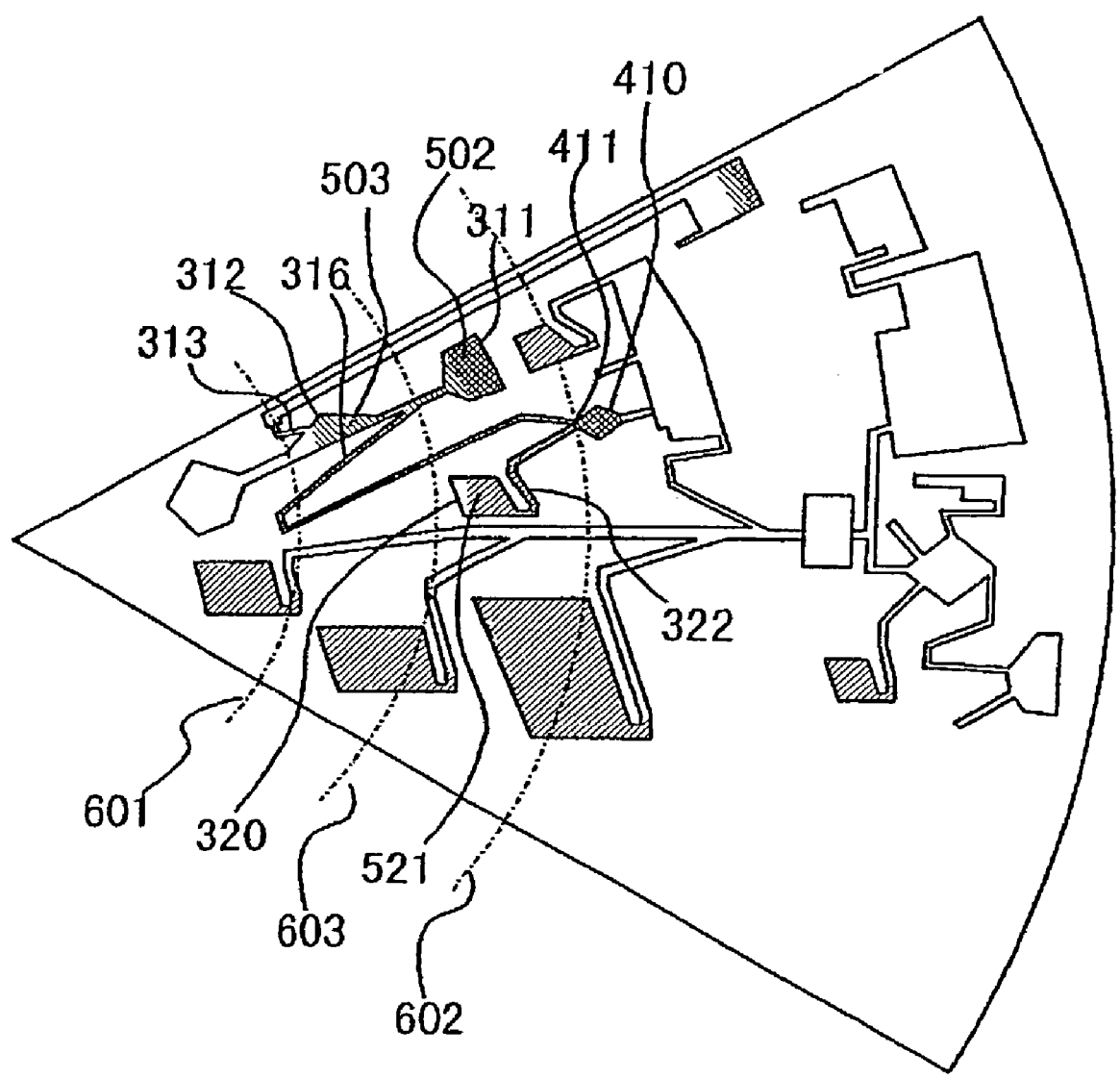
FIG. 9 illustrates the operation of the flow passage portion when blood serum is mixed with a lysis solution according to the invention.

A lysis solution 521 for lysing the membrane protein of a virus in blood serum is dispensed into a lysis solution container 320. After the lid of the lysis solution ventilation hole 221 is perforated by the perforator 13, the motor is rotated, so that the lysis solution 521 flows from the lysis solution container 320 to the mixing portion 410 via the lysis solution backward passage 322 by centrifugal force. As the innermost portion of the blood serum (which is located at the radius position 601 upon completion of separation of blood serum) in the blood-serum quantitative determination container 312 is located more towards the center of rotation than the mixing-portion entrance 411 (at the radius position 602), the blood serum in the blood serum quantitative determination container 312 and that in the blood serum capillary tube 316 flow into the mixing portion 410 via the mixing-portion entrance 411 by the head difference due to centrifugal force (FIG. 9). The mixing portion 410 includes a member for mixing the blood serum and the lysis solution. Examples of the member include a porous filter made of resin, glass or paper, fibers, and silicon or metal projections made by etching or machining.

Figure 10:
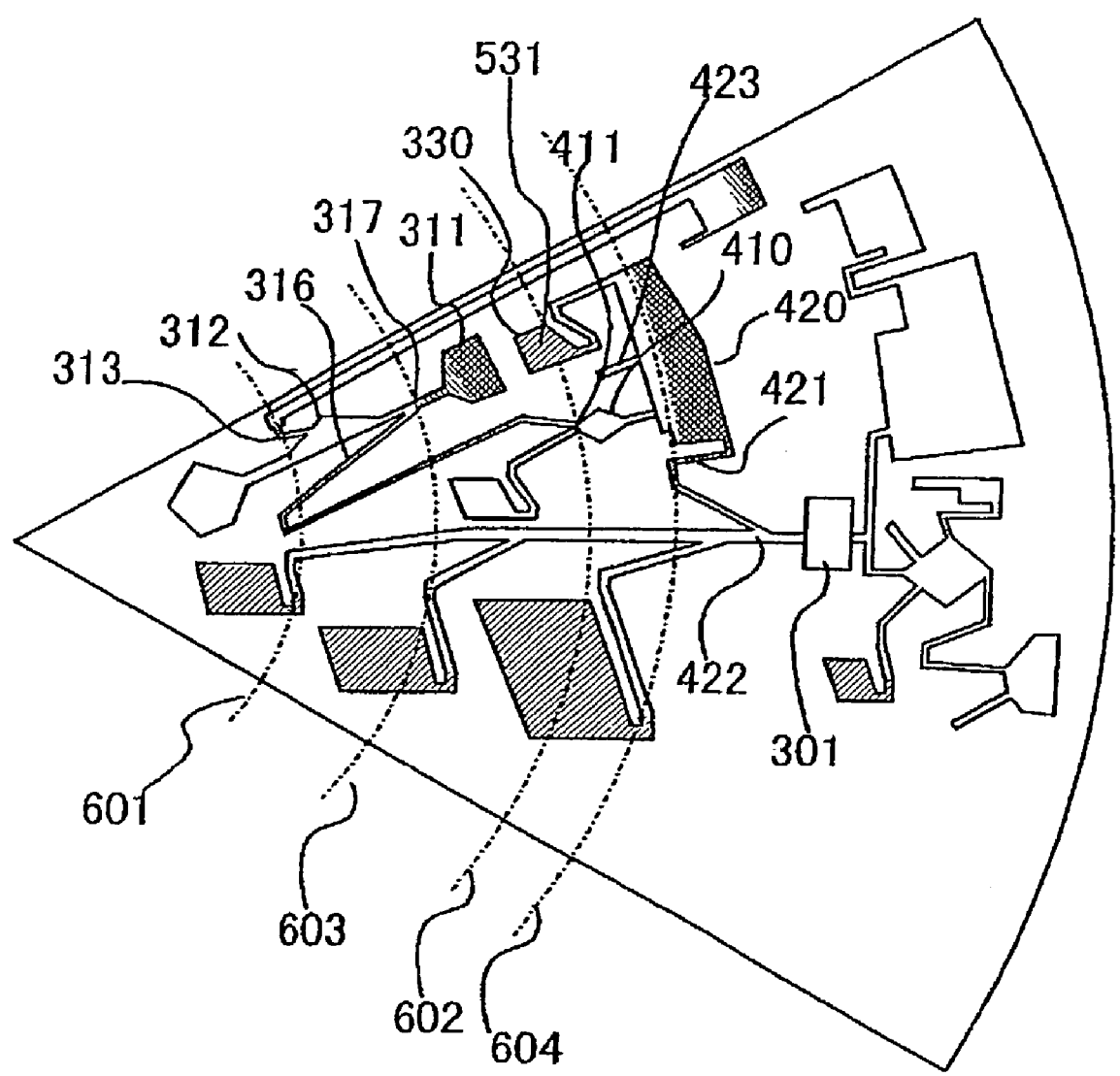
FIG. 10 illustrates the operation of the flow passage portion when blood serum is mixed and reacted with a lysis solution according to the invention.

The blood serum and the lysis solution are mixed in the mixing portion 410 and caused to flow into a reaction container 420 (FIG. 10). The reaction container 420 has a reaction-container ventilation passage 423, and the reaction-container ventilation hole 222 is disposed in the upper cover 20 at a position corresponding to the innermost portion of the reaction-container ventilation passage 423, thus allowing free passage of air into and out of the reaction container 420. Because a branching portion 317 (radius position 603) branching from the blood serum quantitative determination container 312 to the blood serum capillary tube 316 is located more towards the center than the mixing-portion entrance 411 (radius position 602), all of the blood serum in the blood serum capillary tube 316 is caused to flow out to the mixing portion 410 by a siphon effect. At the same time, the blood serum in the blood serum quantitative determination container 312 is caused to flow to the blood serum capillary tube 316 due to centrifugal force, so the blood serum flows into the mixing portion 410 until the liquid level of the blood serum in the blood serum quantitative determination container 312 reaches the branching portion 317 (radius position 603). When the liquid level of the blood serum has reached the branching portion 317, air enters the blood serum capillary tube 316 and the flow stops when the tube is empty. Thus, the blood serum that exists in the blood serum quantitative determination container 312, in the thin overflow passage 313, and in the blood serum capillary passage 316 between the radius positions 601 and 603 upon completion of blood serum separation is caused to flow into the mixing portion 410 and mixed there with the lysis solution.

Thus, by designing the blood serum quantitative determination container 312, the thin overflow passage 313, and the blood serum capillary passage 316 between the radius positions 601 and 603 to have a predetermined volume (required quantity of blood serum), the blood serum to be used for analysis can be quantitatively determined even when the ratio of blood serum with respect to whole blood is different for each blood sample. For example, when the blood cell storage container has a volume of 250 µl and the required blood serum volume is 200 µl, if 500 µl of whole blood is dispensed, 50 µl of whole blood overflows into the whole blood disposal container 315, the remaining 450 µl is separated into blood serum and blood cells, and 200 µl of the separated blood serum flows into the mixing portion 410. Namely, the device according to the invention can analyze a whole blood sample containing 200 µl or more of blood serum with respect to 450 µl of whole blood. With regard to whole blood with a small ratio of blood serum, the volume of the blood cell storage container can be increased to increase the volume of the whole blood sample.

In the reaction container 420, the blood serum and the lysis solution that have been mixed react with each other. The liquid level in the reaction container 420 after the mixture of blood serum and lysis solution has flowed into the reaction container 420 is located more towards the periphery than the innermost portion (radius position 604) of the reaction solution passage 421. Thus, the mixture cannot go beyond the innermost portion of the reaction flow passage and is therefore retained in the reaction container 420 during rotation.

The lysis solution acts to elute nucleic acids from a virus or bacterium in blood serum by lysing their membranes. Further, the lysis solution facilitates the adsorption of the nucleic acids on a nucleic acid binding member 301, which is referred to as a captor by the invention. Examples of the reagents include guanidine hydrochloride for lysing and adsorbing DNA, and guanidine thiocyanate for RNA. The nucleic acid binding member may be made of a porous member of quartz or glass, or a fiber filter.

Figure 11:
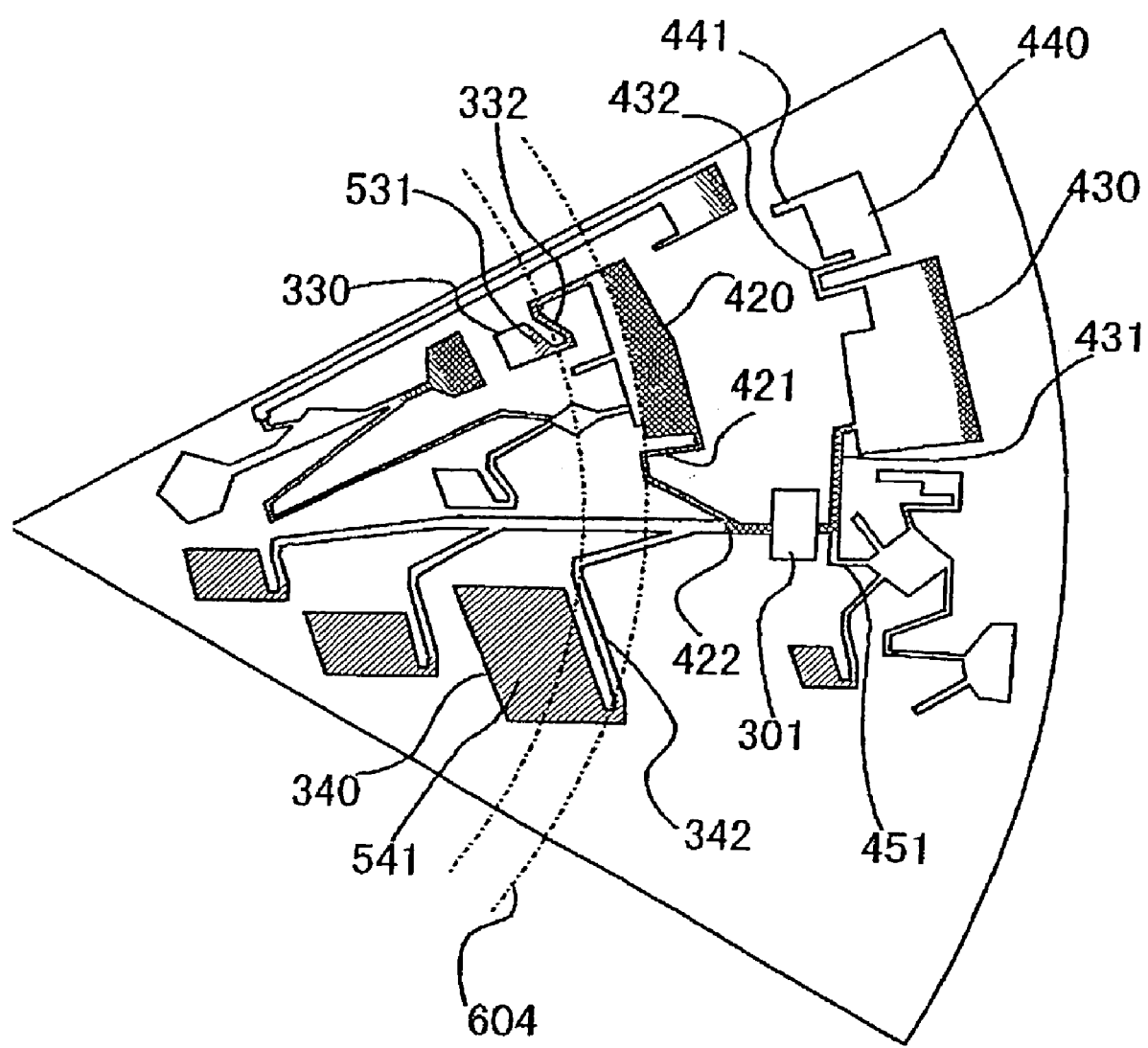
FIG. 11 illustrates the operation of the flow passage portion when an additional solution is added according to the invention.

After the blood serum and the lysis solution are retained in the reaction container 420, the motor 11 is stopped, and the lid of an additional solution ventilation hole 231 is perforated by the perforator 13 in order to supply air to an additional solution container 330. As the motor 11 is rotated again, additional solution 531 flows out of the additional solution container 330 to the reaction container 420 via an additional solution passage 332, by centrifugal force. As a result, the liquid level of the mixture in the reaction container is shifted towards the center of the disc (FIG. 11). As the liquid level reaches the innermost portion (radius position 604) of the reaction solution passage 421, the mixture flows beyond the innermost portion of the reaction solution passage into the nucleic acid binding member 301 via a merging passage 422. The additional solution may be the lysis solution mentioned above, for example.

Depending on samples, the mixture has good wettability against the wall surface, so that the mixture may flow within the reaction solution passage 421 due to capillary action when the disc is stationary. In such a case, no additional solution 531 is required.

As the mixture of lysis solution and blood serum passes the nucleic acid binding member in the above-described manner, the nucleic acids are adsorbed on the nucleic acid binding member. The mixture further flows into a waste liquid storage container 430 via a waste liquid passage 431. A plurality of containers and passages are provided downstream of an eluting solution passage 451, and perforations are created in a later step to supply air into these containers. However, when the mixture passes the nucleic acid binding member 301, the containers are sealed, so that the mixture does not flow into the eluting solution passage 451. The waste liquid container 430 is communicated via a pressure control passage 432 to a pressure control container 440. The pressure control container 440 is provided with a pressure control ventilation passage 441, and a pressure control ventilation hole 223 is provided in the upper cover 20 at a position corresponding to the innermost portion of the pressure control ventilation passage 441. Thus, air can freely enter and exit the pressure control container 440.

Figure 12:
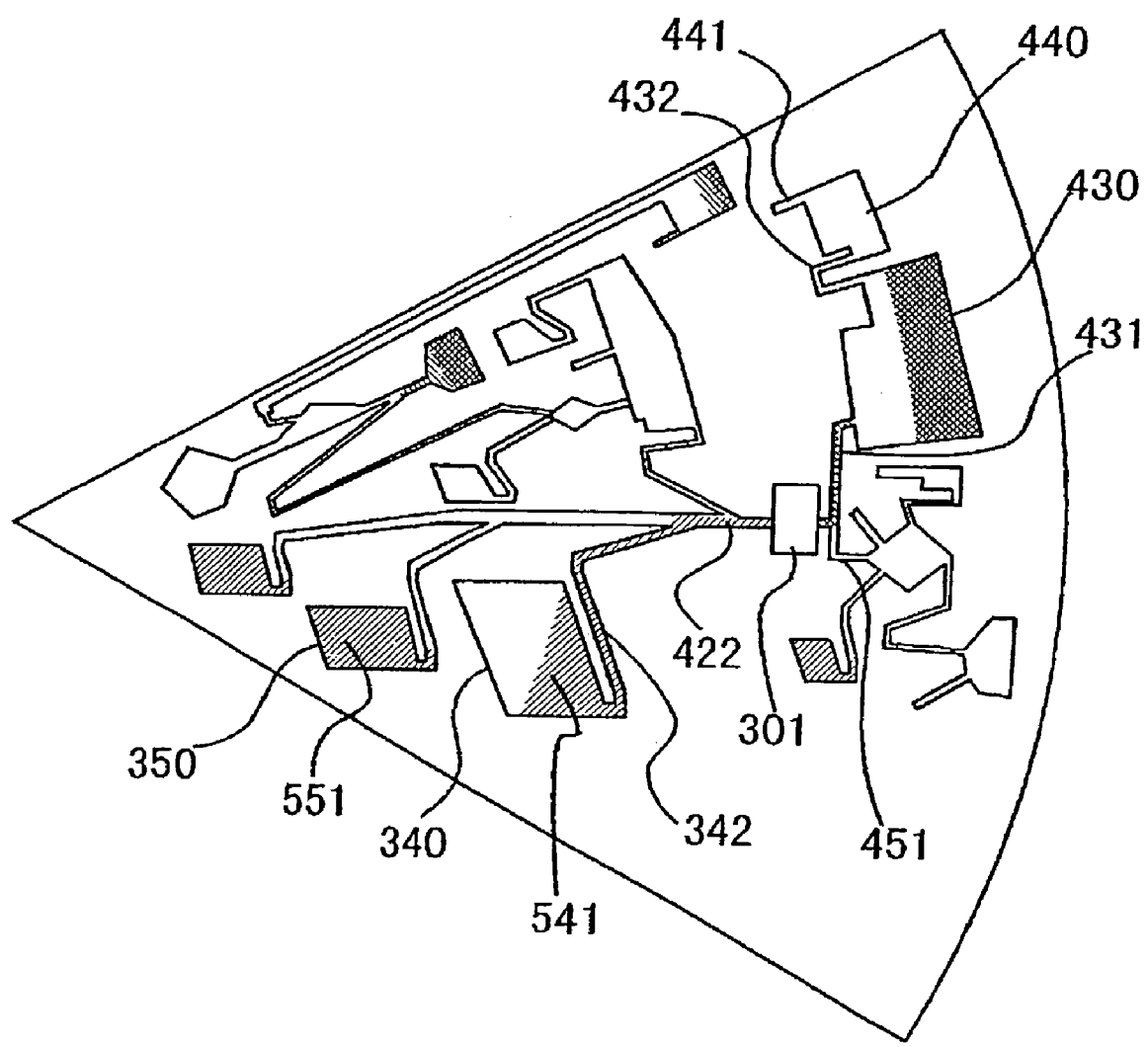
FIG. 12 illustrates the operation of the flow passage portion during washing according to the invention.

Then, the motor 11 is stopped, and the lid of a first washing solution ventilation hole 241 is perforated by the perforator 13 in order to supply air to a first washing solution container 340. As the motor 11 is rotated again, a first washing solution 541 flows out of the first washing solution container 340 due to centrifugal force. The first washing solution 541 further flows into the nucleic acid binding member 301 via a first washing solution backward passage 342, and washes unwanted components, such as protein, that have attached to the nucleic acid binding member 301 (FIG. 12). The first washing solution may be the above-mentioned lysis solution, or such solution with a reduced salt concentration.

The waste liquid after the washing flows via the waste liquid passage 431 into the waste liquid storage container 430, as did the mixture.

The same washing operation is repeated several times. For example, after the first washing solution, the lid of a second washing solution ventilation hole 241 is perforated by the perforator 13 to supply air to a second washing solution container 350, with the motor stopped. Then, the motor 11 is again rotated, and unwanted components such as salts that are attached to the nucleic acid binding member 301 are washed. The second washing solution may be ethanol or an aqueous solution of ethanol.

The same washing operation may be repeated further if necessary.

During the washing step, as each washing solution flows to the waste liquid storage container 430 via the waste liquid passage 431, part of the eluting solution passage 451, particularly the areas near the branching portion connecting to the waste liquid passage, may possibly be contaminated. As will be described later, because the nucleic acids eluted from the nucleic acid binding member 301 pass the eluting solution passage 451, it is desirable to wash the eluting solution passage 451 as well.

In the first embodiment shown in FIGS. 6 to 17, two kinds of washing solutions, that is, the first washing solution 541 and a second washing solution 551, are used for washing. In the following, the example of washing the eluting solution passage 451 with the second washing solution will be described.

Figure 13:
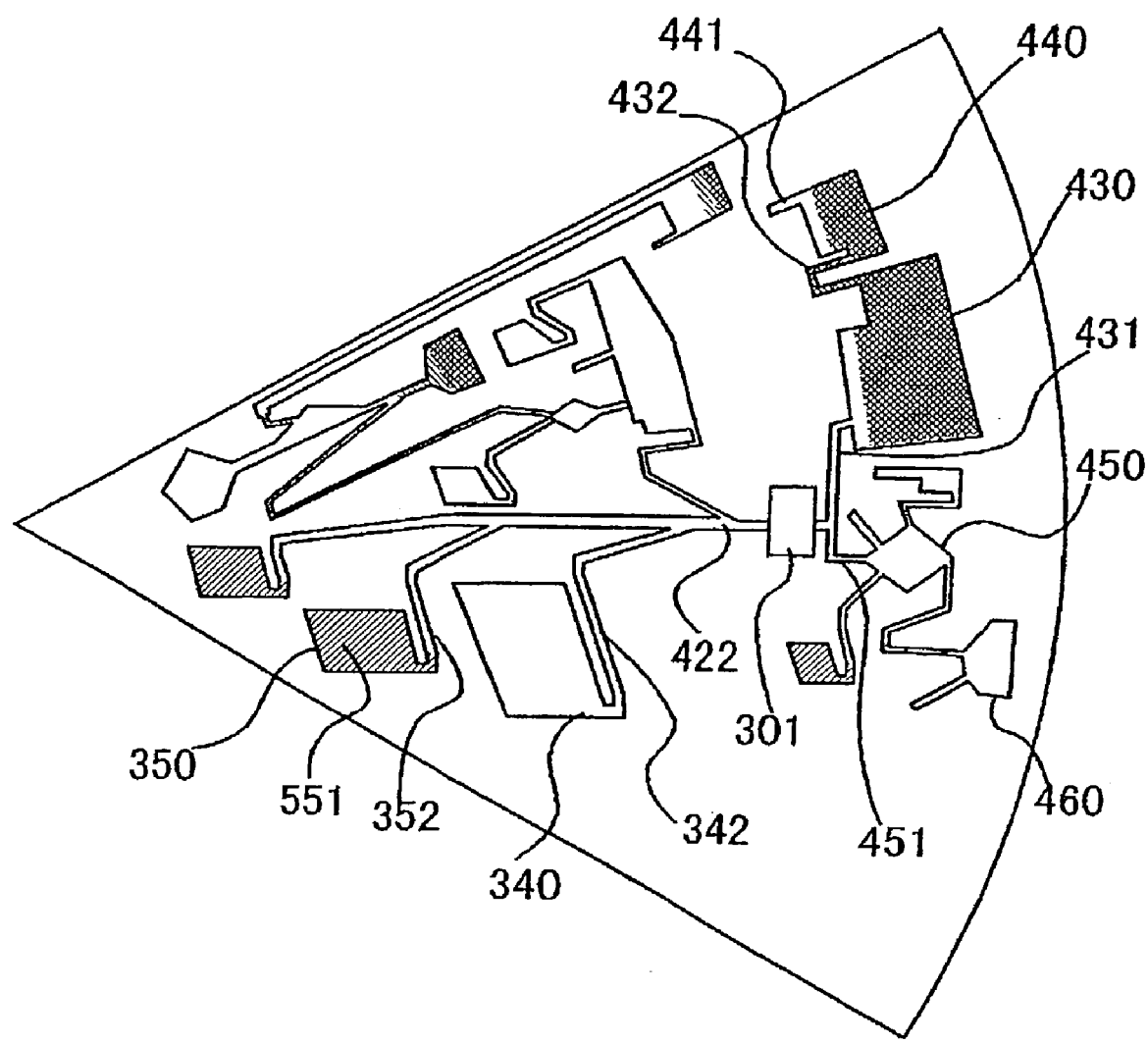
FIG. 13 illustrates the operation of the flow passage portion during washing according to the invention.

FIG. 13 shows the state in which all of the first washing solution has passed through the waste liquid passage 431. The waste liquid has overflowed from the waste liquid storage container 430 to the pressure control passage 440 via the pressure control passage 432. The motor is once stopped, and the lid of the second washing solution ventilation hole 241 is perforated by the perforator 13 to deliver air into the second washing solution container 350. The lid of a detection container ventilation hole 272 is perforated in order to communicate a detection container 450 with the outside. The lid of a final washing-solution ventilation hole 273 is perforated in order to communicate a final washing solution disposal container 460 with the outside.

Figure 14:
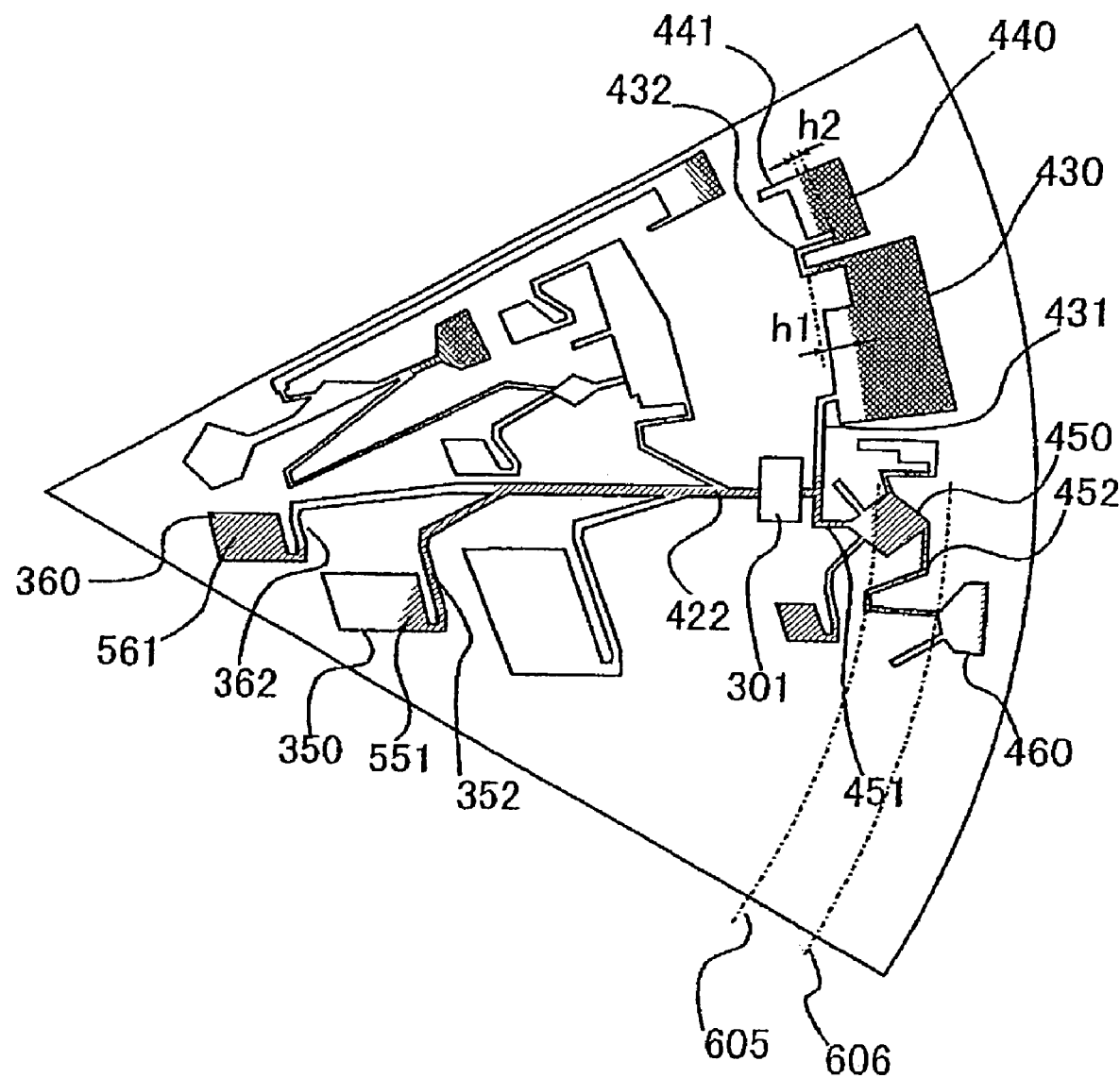
FIG. 14 illustrates the operation of the flow passage portion during washing according to the invention.

As the motor 11 is rotated again, the second washing solution 551 flows out of the second washing solution container 350 due to centrifugal force. The second washing solution 551 further flows into the nucleic acid binding member 301 via a second washing solution backward passage 352, and washes the first washing solution that has attached to the nucleic acid binding member 301 (FIG. 14). The second washing solution that has passed the nucleic acid binding member 301 tends to flow into both the detection container 450 and the waste liquid storage container 340. However, the second washing solution cannot enter the waste liquid storage container 430, due not only to a head difference (h1) that is encountered when the solution is to enter the pressure control passage 432, but also to another head difference (h2) that is required to push air from the pressure control passage 432 into the pressure control container 440. On the other hand, the solution can flow into the detection container 450 virtually resistance-free, because of the ventilation hole created by the above perforation operation. Thus, the second washing solution, after passing through the nucleic acid binding member 301, flows via the eluting solution passage 451 into the detection container 450, which is referred to as an eluting solution carrier by the invention. At the same time, the areas near the branching portion connecting to the waste liquid passage 431 that have been contaminated by the mixture or the first washing solution are washed.

As the second washing solution enters the detection container 450 and as soon as its liquid level reaches the innermost portion (radius position 605) of the washing solution disposal passage 452, the second washing solution begins to flow into the final washing solution disposal container 460. Because the connecting portion (radius position 606) between the washing solution disposal passage 452 and the detection container is located more towards the periphery than the innermost portion (radius position 605) of the passage, once the solution flows into the final washing solution disposal container 460, all of the solution in the detection container 450 tends to be drained due to a siphoning effect. However, minute amounts of the solution that have remained in the nucleic acid binding member 301, for example, could flow into the detection container 450 after drainage is complete. If that happens, the rotation is once stopped, and then re-started after the washing solution disposal passage 452 is filled by capillary flow with the solution that has remained in the detection container 450, so that the solution remaining in the detection container 450 is drained out to the final washing solution disposal container 460 again by a siphoning effect. Accordingly, with regard to the final washing solution, it is preferable to repeat the procedure of rotation and stop twice after creating the ventilation hole.

After the nucleic acid binding member 301 is thus washed so that only the nucleic acids are adsorbed thereon, a step of eluting the nucleic acids is carried out.

Figure 15:
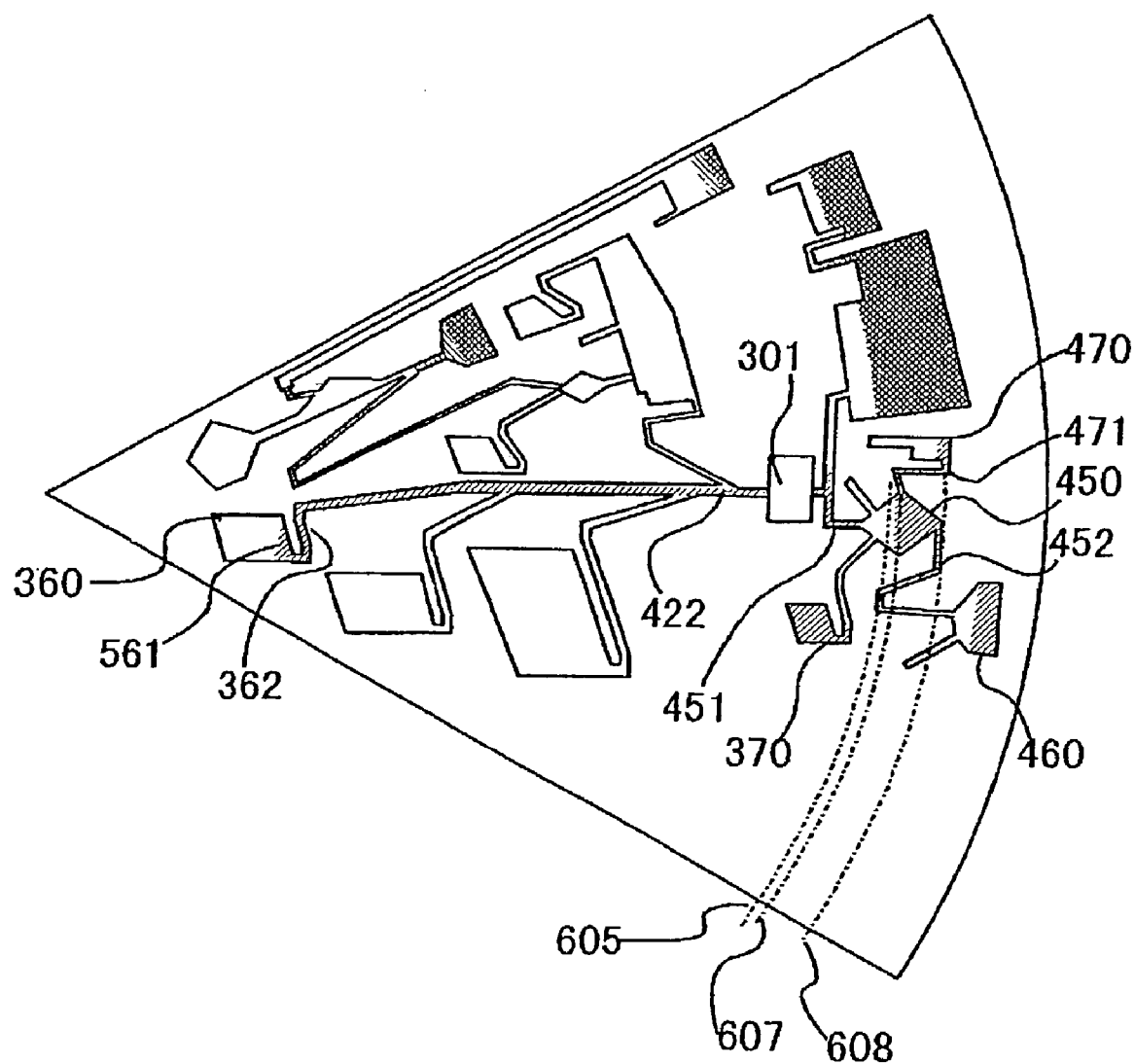
FIG. 15 illustrates the operation of the flow passage portion when the flow of the eluting solution is controlled according to the invention.

Specifically, the lid of an eluting solution ventilation hole 261 is perforated by the perforator 13 to supply air to the eluting solution container 360, with the motor stopped. Further, the lid of an eluting solution-disposal ventilation hole 274 is perforated to communicate an eluting solution disposal container 470, which is referred to as an eluting solution disposal portion by the invention, with the outside. The motor 11 is rotated again, and the eluting solution flows to the nucleic acid binding member 301 (FIG. 15). The eluting solution is a solution for eluting nucleic acids from the nucleic acid binding member 301, and it may be water or an aqueous solution with pH adjusted between 7 and 9. The solution is preferably heated to 40° C. or higher for facilitating elution. The heating may be carried out by irradiating the eluting solution container 360 from above with light by means of the upper optical device 14 shown in FIG. 1.

Figure 16:
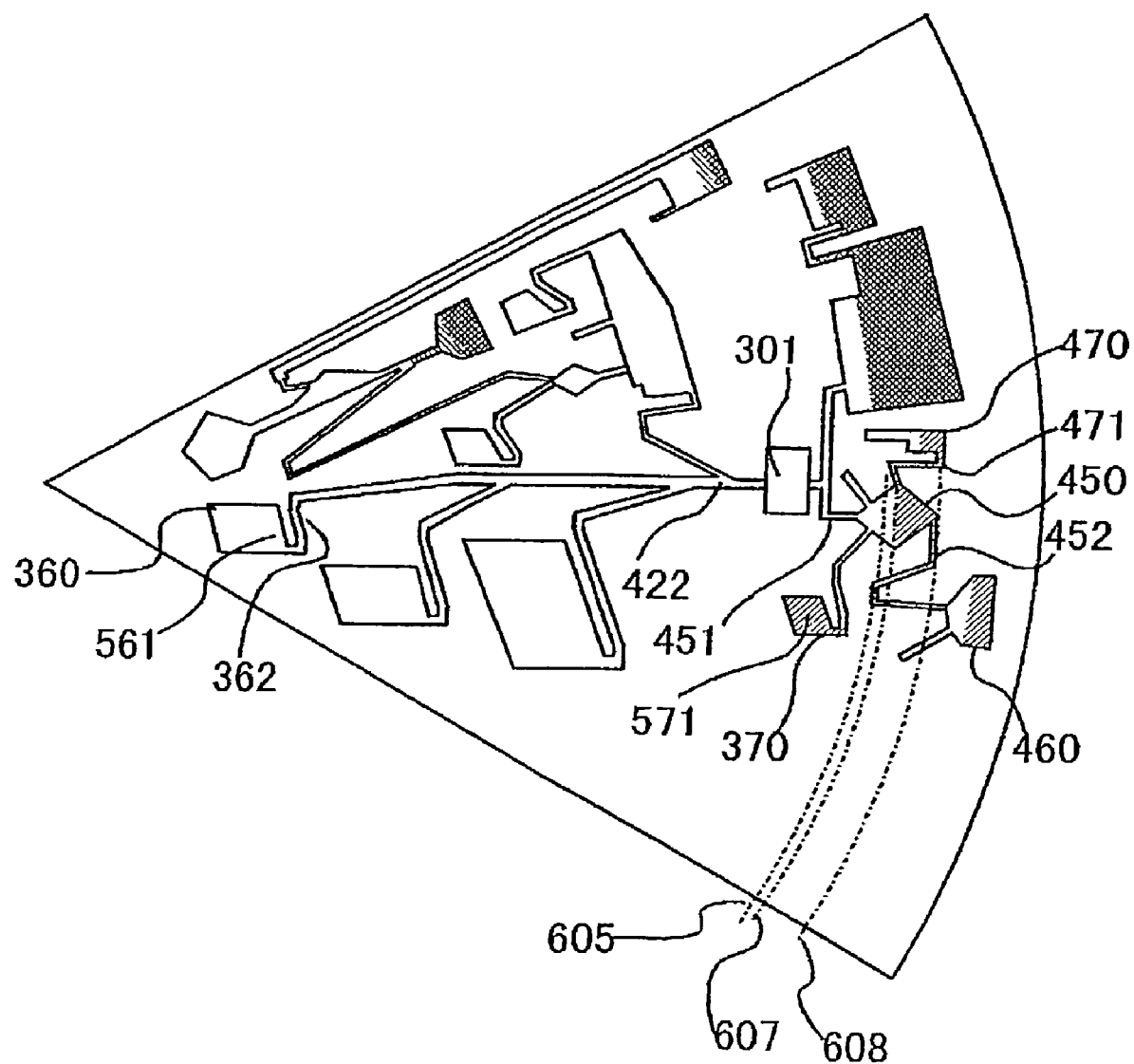
FIG. 16 illustrates the operation of the flow passage portion during elution and an operation to maintain a certain quantity of eluting solution according to the invention.

After passing through the nucleic acid binding member 301, the eluting solution flows into the detection container 450 via the eluting solution passage 451. As the eluting solution disposal container 470 is communicated with the outside by perforation as described above, the eluting solution flows out to the eluting solution disposal container 470 via an eluting solution disposal passage 471. Because the connecting portion (radius position 607) between the eluting solution disposal passage 471 and the detection container 450 is located more towards the center than the connecting portion (radius position 608) connecting to the eluting solution disposal container 470, the eluting solution that exists in the detection container 450 beyond the radius position 607 towards the center is drained to the eluting solution disposal container 470 by a siphoning effect. Thus, a certain quantity of the eluting solution containing nucleic acids can be carried in the detection container 450 (FIG. 16).

Figure 17:
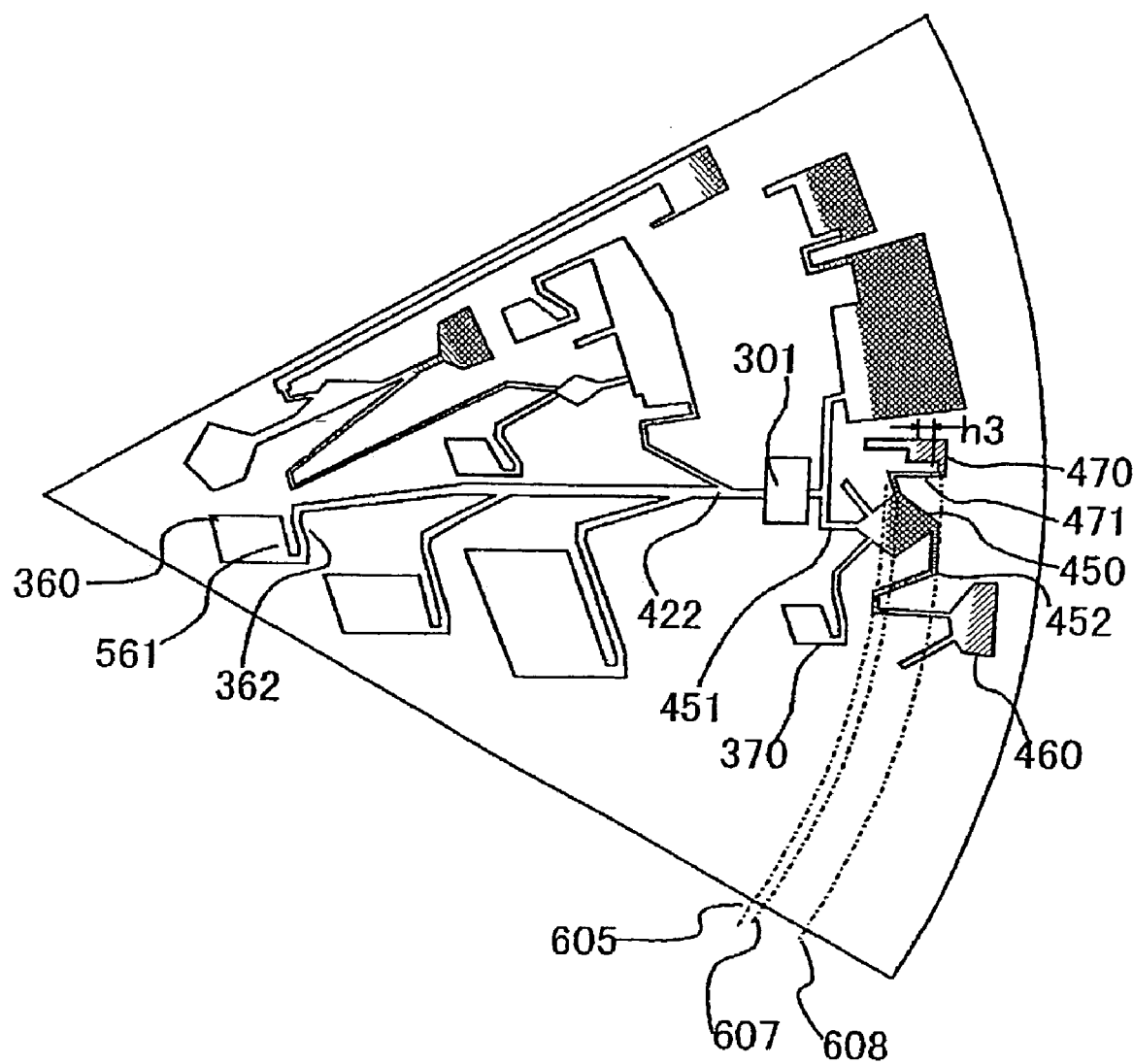
FIG. 17 illustrates the operation of the flow passage portion during amplification according to the invention.

Thereafter, with the motor stopped, the lid of a detection solution ventilation hole 271 is perforated by the perforator 13 to supply air to the detection solution storage container 370. The motor 11 is rotated again, and a detection solution 571 flows to the detection container 450 (FIG. 17). The detection solution is a reagent for amplifying and detecting nucleic acids, and it includes deoxynucleoside triphosphate, DNA synthetic enzyme, or fluorescence reagent, for example. Depending on the method of amplification, the detection solution may be heated from above through the detection container 450 with the upper optical device 14.

Next, the lower optical device 15 is transported below the detection container 450 to detect the amount of fluorescence, for example.

Figures 19, 20:
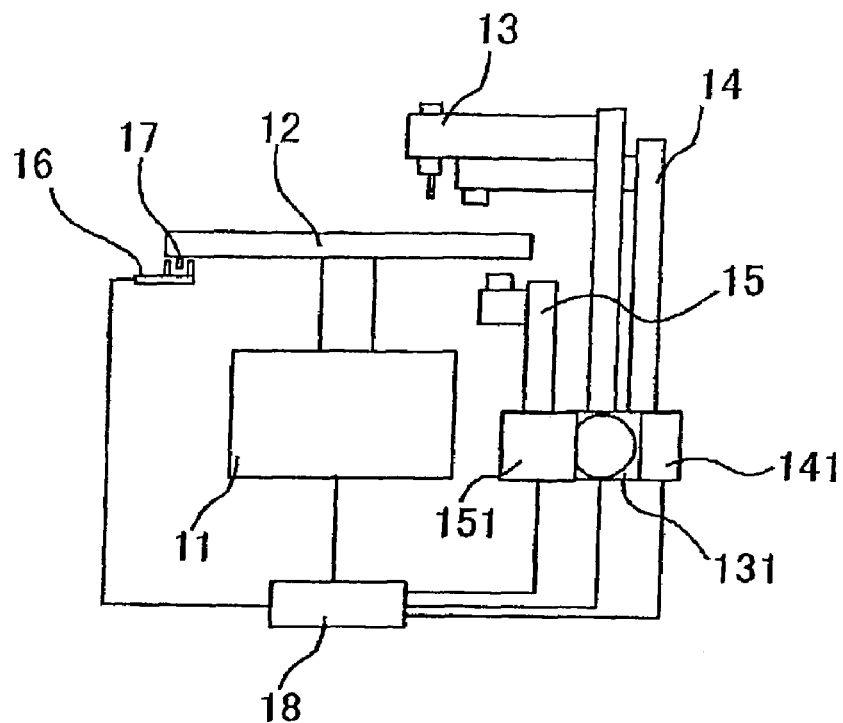
FIG. 19 shows a circuit diagram of a positioning mechanism according to the invention.
FIG. 20 shows a timing chart for a positioning operation according to the invention.

The carrier disc 12 must be stopped at predetermined positions during perforation, heating, and detection. As shown in FIG. 19, the carrier disc 12 is provided with a positioning protrusion 17. This allows the rotation position of the carrier disc to be detected by a position detector 16, so that the rotation of the motor 11, the rotation and vertical movement of the perforator 13, and the rotation, irradiation, and detection by the upper and lower optical devices 14 and 15 can be controlled by a controller 18.

FIG. 20 shows the operational timing of the perforator 13, for example. The rotational speed of the carrier disc 12 is lowered after the whole blood or each reagent has been moved, and a slow rotation speed for positioning is maintained. As the position detector 16 detects the positioning protrusion 17, the carrier disc 12 is stopped. The perforator 13 is then lowered to perforate the lid of the ventilation hole for each reagent storage container, and then raised again. After perforation, the carrier disc 12 rotates at such a slow speed that the reagents do not flow out of the individual reagent storage containers after perforation. The carrier disc 12 comes to a stop at the position for the next analysis disc, that is, after rotating 60° in the case where six analysis discs are mounted. The same perforation operation is repeated. The location of the analysis disc can be known by irradiating light from above with the lower optical device through a flow passage optical window 490 and examining the reflected light. After all of the analysis discs have been perforated, the carrier disc is rotated at high speed to cause the reagents to flow.

In accordance with the present embodiment, there is no need to provide a valve in flow passages for controlling the flow of the sample and each reagent. Thus, the problem of solution remaining at the valve portion in the course of the flow passages does not occur, and the contamination by reagents in the pre-process can be prevented. Accordingly, specific components in a liquid sample, such as nucleic acids, can be extracted with high purity and analyzed accurately.

Embodiment 2

While in Embodiment 1 blood serum is separated from whole blood, and nucleic acids in a pathogen such as a virus or bacterium contained in the separated blood serum are extracted and analyzed, nucleic acids in white blood cells may be extracted from whole blood and analyzed.

Referring to FIGS. 21 to 28, an embodiment of a genetic analysis apparatus for extracting nucleic acids in white blood cells from whole blood and analyzing them will be described.

The overall structure of the genetic analysis apparatus according to the invention is similar to that shown in FIG. 1. Instead of the analysis disc 2 for the extraction and analysis of nucleic acids in a pathogen such as a virus or bacterium, a white blood cell analysis disc 3 is employed for extracting nucleic acids in white blood cells and analyzing them.

Figure 21:
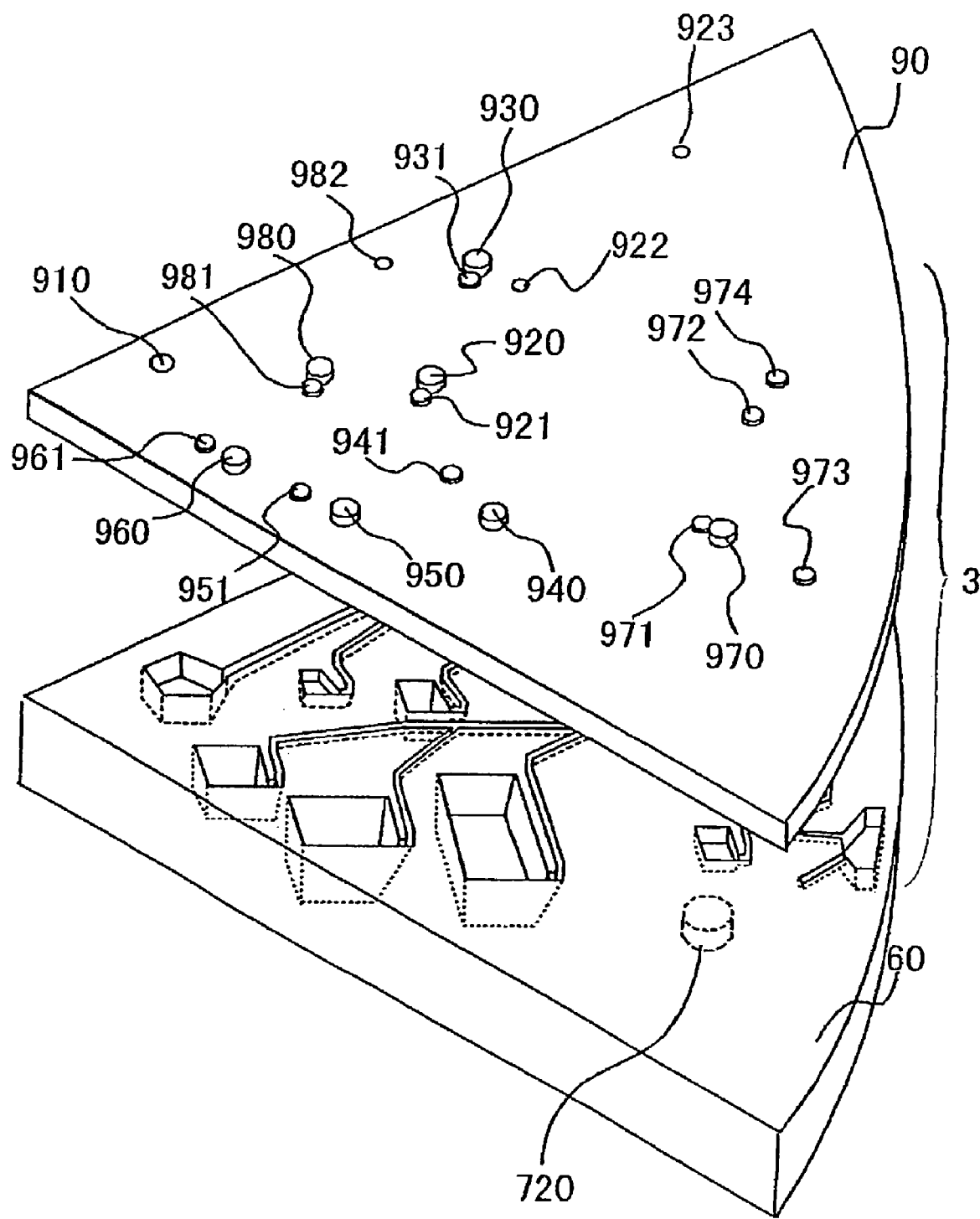
FIG. 21 shows the structure of an analysis disc according to the invention.

FIG. 21 shows the structure of the white blood-cell analysis disc 3, which is made of an upper cover 90 and a flow passage portion 60 joined together. The upper cover 90 comprises a sample inlet 910, a plurality of reagent inlets 920, 930, 940, 950, 960, 970, and 980, a plurality of ventilation holes 922, 923, and 982, and a plurality of lidded-ventilation holes 921, 931, 941, 951, 961, 971, 972, 973, 974, and 981. The flow passage portion 60 includes a positioning hole 720, containers, and flow passages, which will be described later. The white blood cell analysis disc 3 is positioned when the protrusion 121 on the carrier disc 12 shown in FIG. 1 fits into the positioning hole 720.

Figure 22:
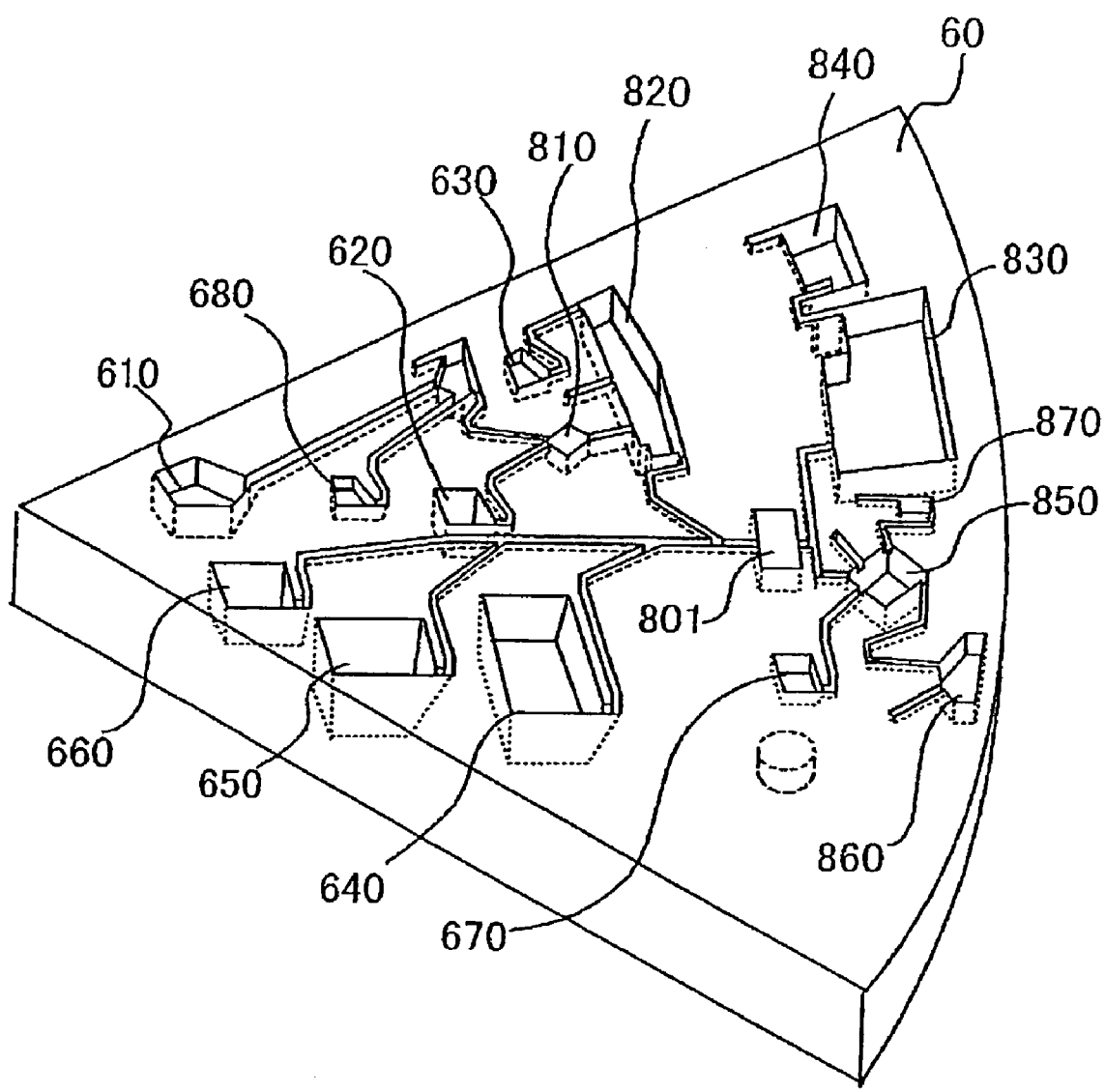
FIG. 22 shows the structure of a flow passage portion according to the invention.

FIG. 22 shows the structure of the flow passage portion 60. In this embodiment, nucleic acids contained in white blood cells are extracted from whole blood. An extraction solution is then quantitatively determined and analyzed after adding a detection reagent thereto.

Figure 23:
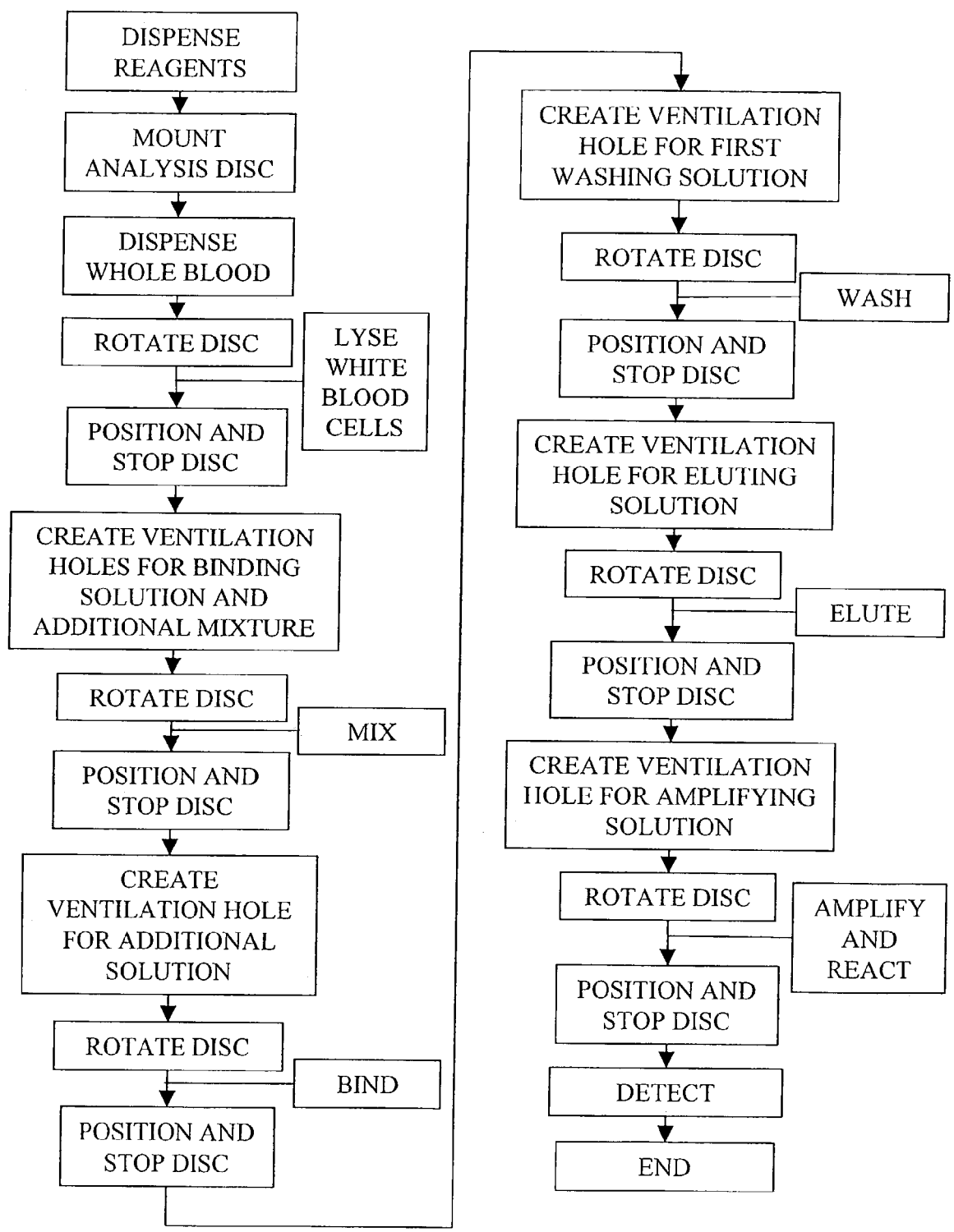
FIG. 23 shows the flow of an analysis operation according to the invention.
Figure 24:
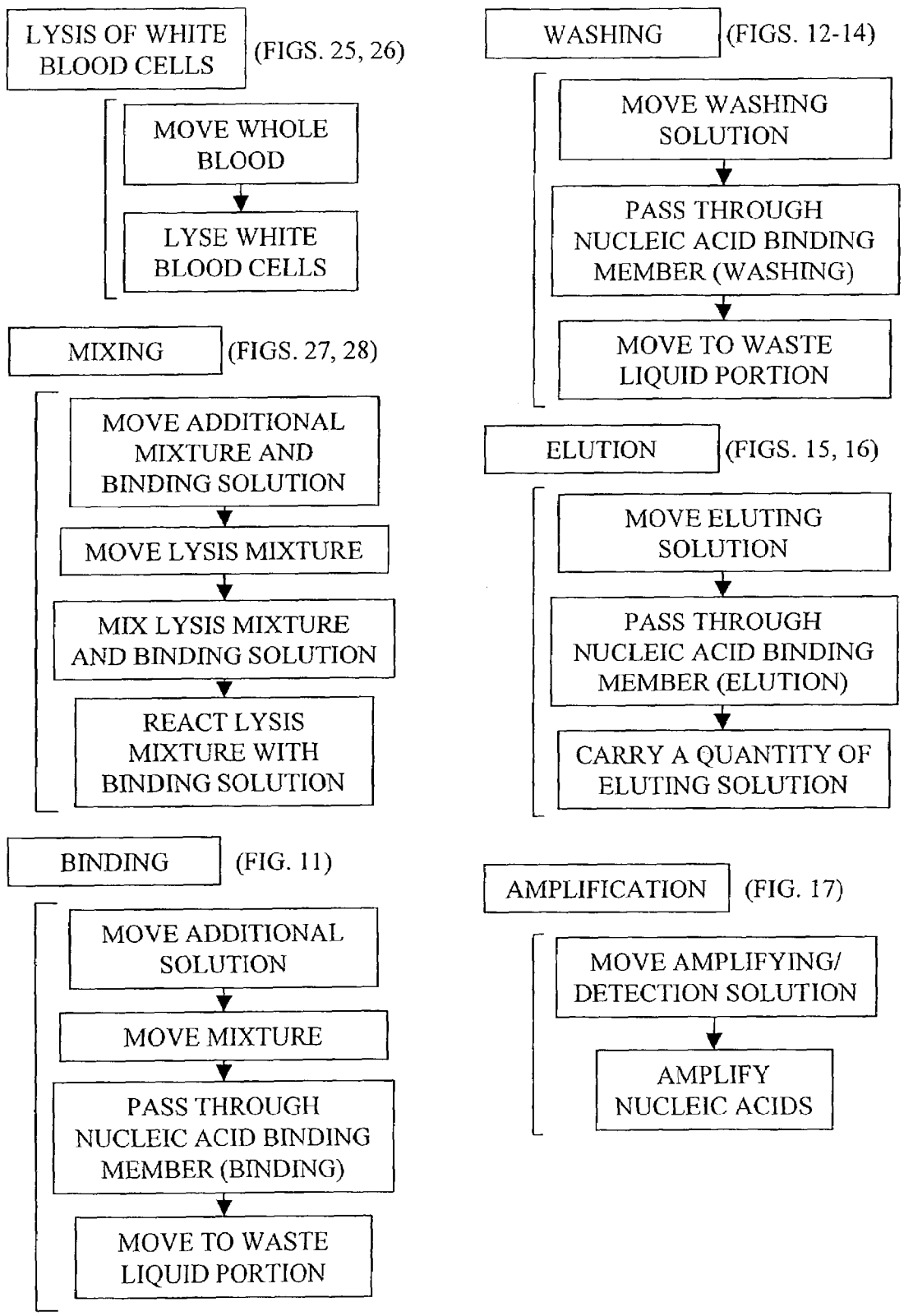
FIG. 24 shows the individual analysis operations and illustrates their correspondence to the individual figures.

Hereafter, the operation for extracting and analyzing nucleic acids in the case of using whole blood as a sample will be described. FIGS. 23 and 24 show the flow of extraction and analysis operations, while FIGS. 25 to 28 show the various states of flow of solutions in the flow passage portion 60 on a step by step basis.

The operator dispenses the reagents into the individual reagent containers 620, 630, 640, 650, 660, 670, and 680 via the reagent inlets 920, 930, 940, 950, 960, 970, and 980 in the upper cover 90 of the analysis disc 3, and then closes the lids. After the reagents are introduced into as many analysis discs as are necessary depending on the number of analyses, the analysis discs are mounted on the carrier disc 12.

Figure 25:
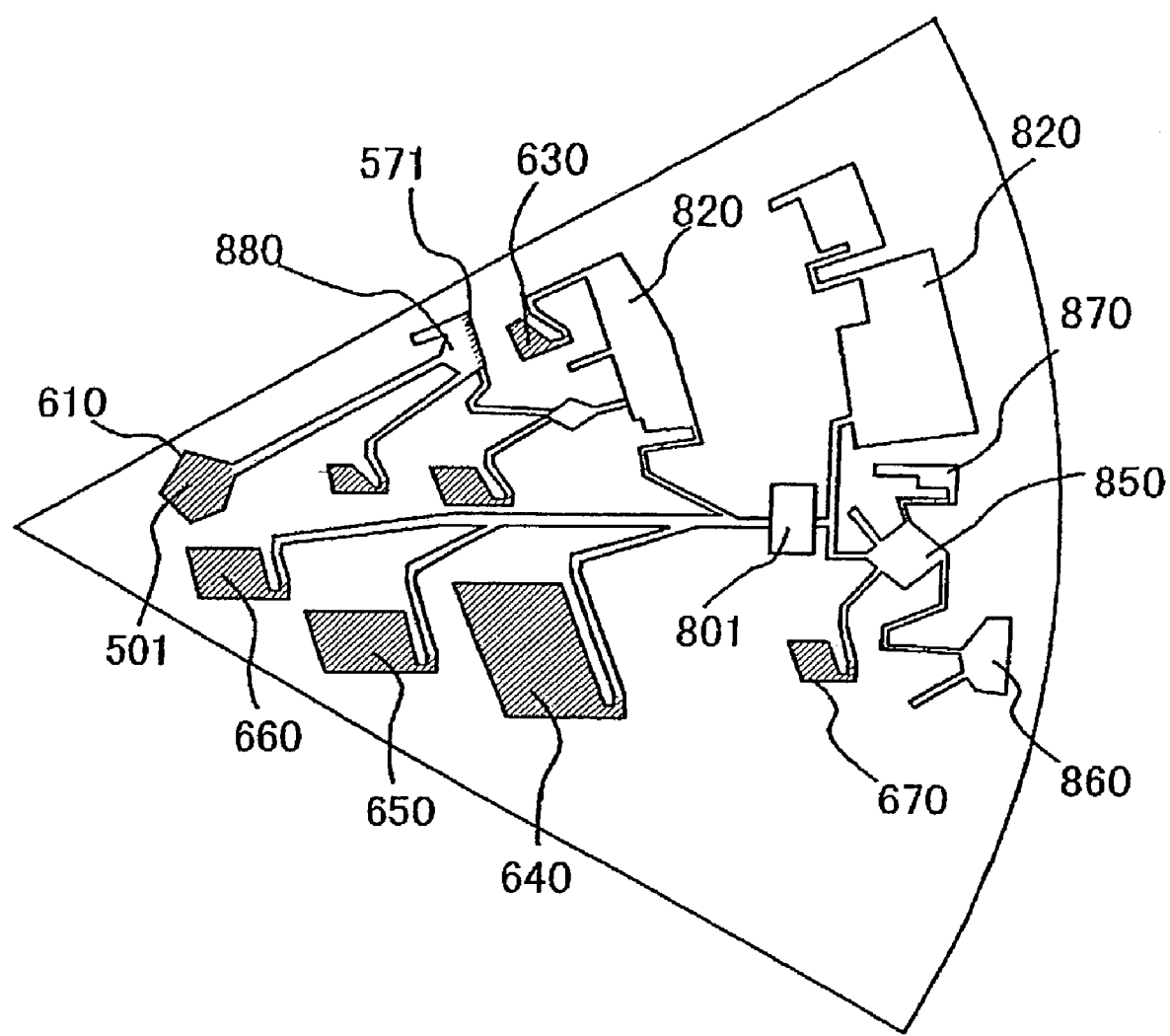
FIG. 25 illustrates the operation of the flow passage portion during the lysing of white blood cells according to the invention

Then, whole blood drawn by a vacuum blood-collecting tube or the like is introduced into a sample container 610 via the sample inlet 910 (FIG. 25).

Figure 26:
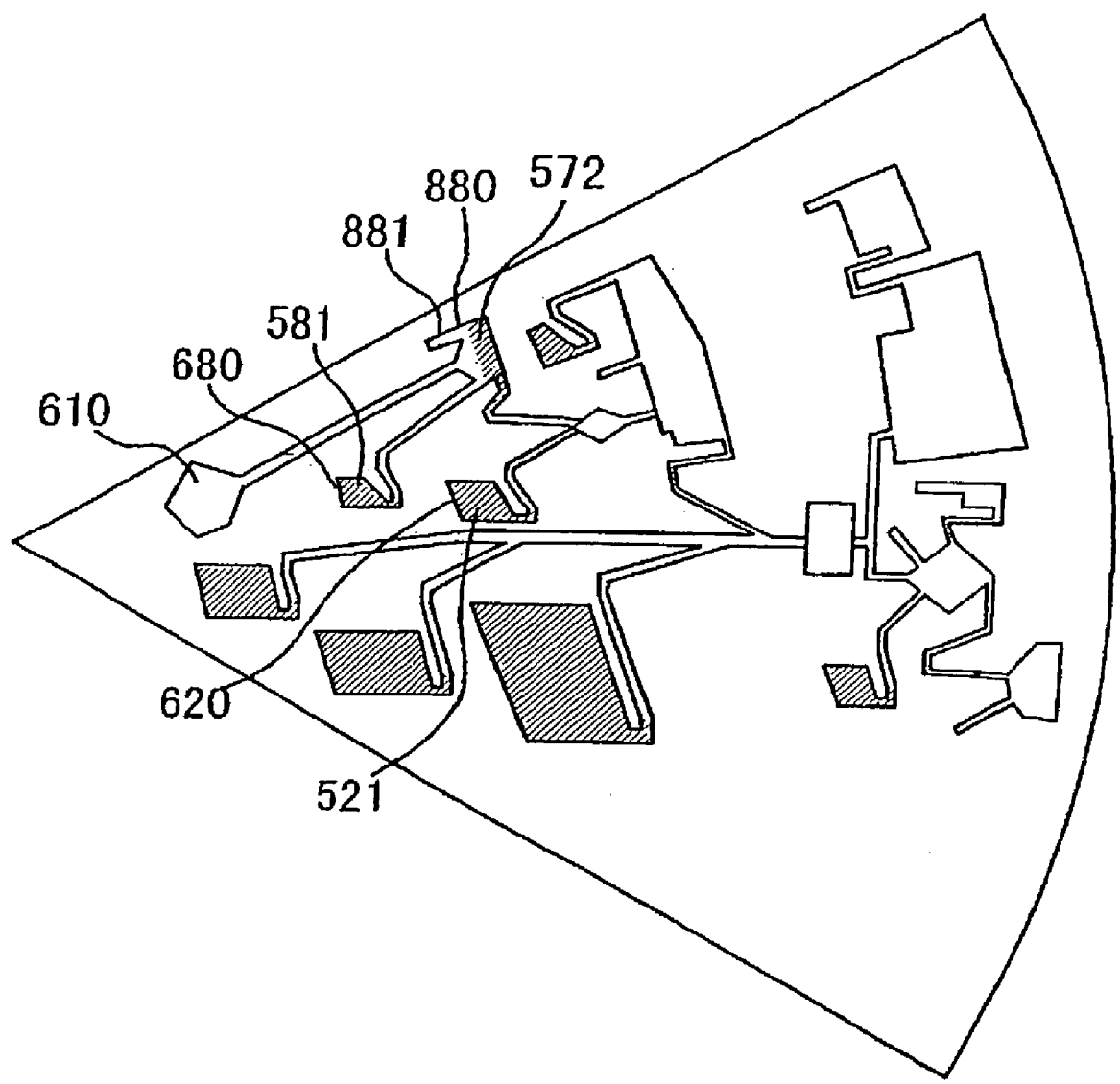
FIG. 26 illustrates the operation of the flow passage portion during the lysing of white blood cells according to the invention.

After the introduction of the whole blood 501, the carrier disc 12 is rotated by the motor 11. The whole blood introduced into the sample container 610 flows towards the periphery due to the centrifugal force generated by the rotation of the carrier disc 12. The whole blood further flows into a lysis container 880, where it mixes with a lysis solution 571 in the lysis container 880, thus lysing the white blood cells in the whole blood (FIG. 26). The lysis container 880 is provided with a lysis container ventilation passage 881, and a lysis container ventilation hole 982 is provided in the upper cover 90 at a position corresponding to the innermost portion of the lysis solution ventilation passage 881. Thus, air can freely enter and exit the lysis container 880.

The lysis solution may be protease such as protease K.

During lysis, the lids of the ventilation holes 921, 931, 941, 951, 961, 971, and 981 on the upper cover 90 for the individual reagent containers are closed, as in Embodiment 1, thereby sealing the containers. Further, backward passages are provided, as in the example of FIG. 6, such that the reagents flowing out of the individual reagent containers from the peripheral side can be brought back towards the center. Thus, pressure reduction in the reagent containers is suppressed and generation of bubbles is prevented.

When lysis of white blood cells is complete, the analysis disc 3 is stopped at a predetermined position.

Thereafter, the perforator 13 perforates the lids of the individual ventilation holes above the reagent containers one by one, followed by rotation of the motor 11, which causes the individual reagents to flow by centrifugal force. The cross-section of each reagent container looks as shown in FIG. 18A or 18B, as in Embodiment 1. By perforating the lid of each ventilation hole by the perforator 13, air is allowed to enter each reagent container.

Hereafter, the operation after lysis will be described.

Figure 27:
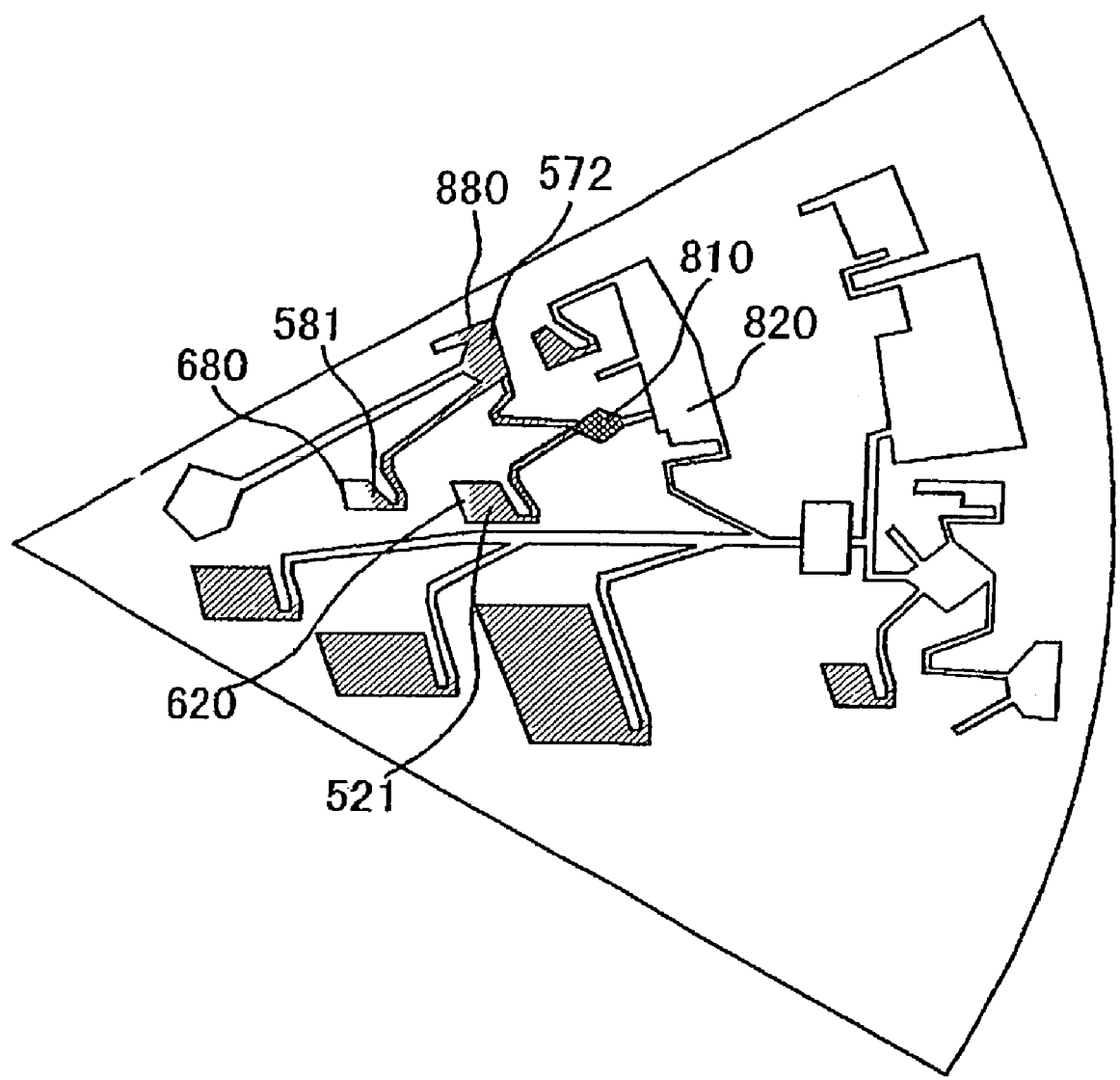
FIG. 27 illustrates the operation of the flow passage portion during the mixing of a lysis mixture and a binding solution according to the invention.

After the perforator 13 has perforated the lids of a binding solution ventilation hole 921 and an additional mixture solution ventilation hole 981, the motor 11 is rotated. As a result, a binding solution 521 and an additional mixture solution 581 flow out of the binding solution container 620 and the additional mixture solution container 680, respectively. The additional mixture solution 581 flows into a lysis container 880, thereby pushing a mixture (lysis mixture 572) of the whole blood 501 and the lysis reagent 571 out of the lysis container 880 into a mixing portion 810. Thus, the binding solution 521 is mixed with the lysis mixture 572 in the mixing portion 810 (FIG. 27).

The mixing portion 810 is made of a member for mixing the lysis mixture and the binding solution. For example, it could be a porous filter of resin, glass, or paper, fibers, or a projection of silicon or metal made by etching or machining.

Figure 28:
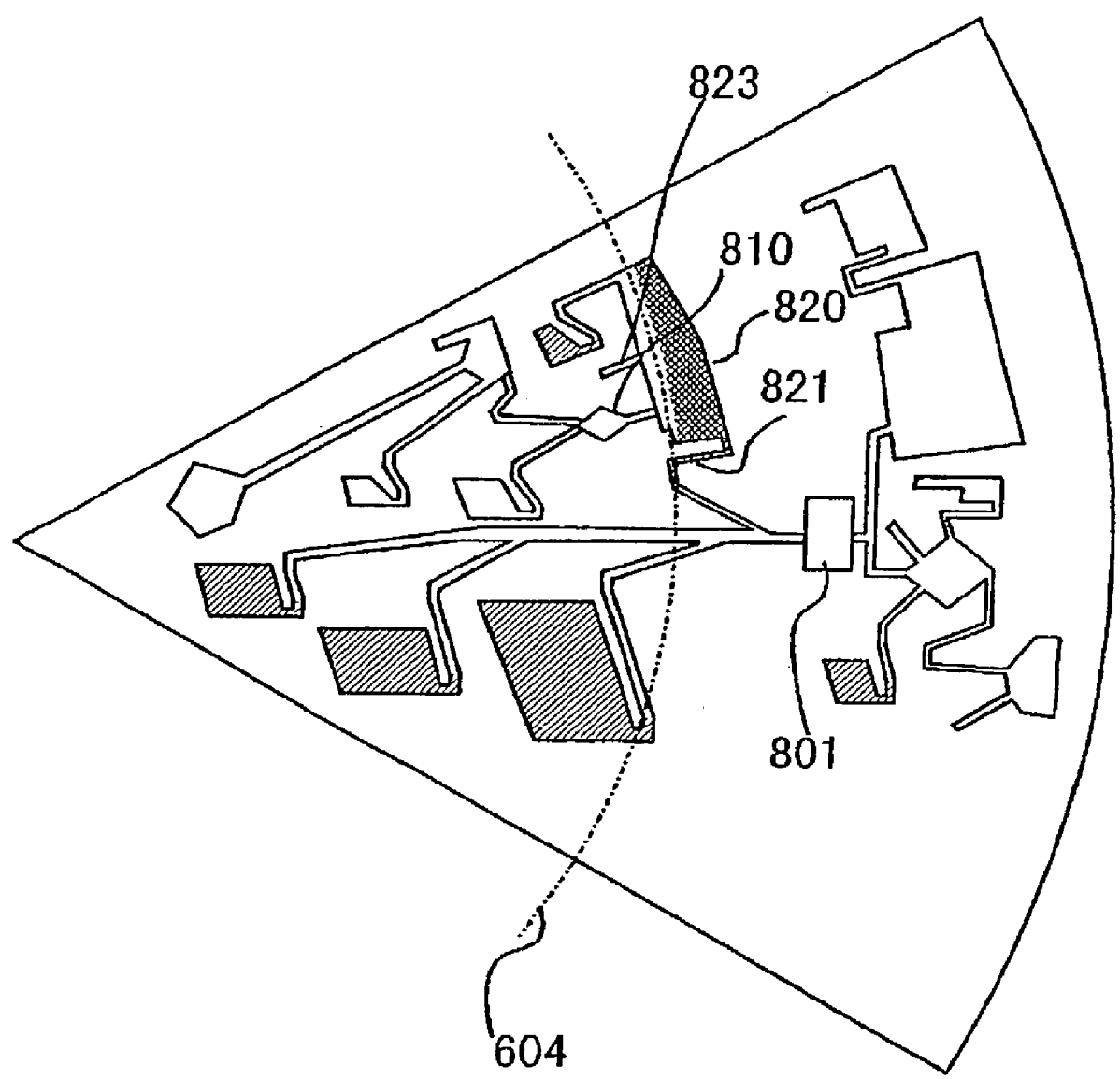
FIG. 28 illustrates the operation of the flow passage portion during the mixing of a lysis mixture and a binding solution according to the invention.

After the lysis mixture 572 is mixed with the binding solution 521 in the mixing portion 810, the resultant mixture flows into a reaction container 820 (FIG. 28). The reaction container 820 is provided with a reaction container ventilation passage 823. Further, a reaction container ventilation hole 922 is provided in the upper cover 90 at a position corresponding to the innermost portion of the reaction container ventilation passage 823. Accordingly, air can freely enter and exit the reaction container 820.

In the reaction container 820, the lysis mixture is reacted with the binding solution. The liquid level in the reaction container 820 after the lysis mixture and the binding solution have moved therein is located more towards the center than the innermost portion (radius position 604) of a reaction solution passage 821 and cannot go beyond the inner portion. Therefore, the mixture can be carried in the reaction container 820 during rotation.

The binding solution facilitates the adsorption of nucleic acids on a nucleic acid binding member 801, which is referred to by the invention as the captor. Examples of such a reagent include guanidine hydrochloride and guanidine thiocyanate. The nucleic acid binding member may be a porous member of quartz or glass, or a fiber filter, for example. The additional mixture solution, which is a solution for pushing out the lysis mixture, is preferably the above-mentioned mixture 521 or the lysis solution 571.

After the additional mixture and the binding solution are carried in the reaction container 820, the same procedure as in Embodiment 1 is carried out. Therefore, regarding the flow states of the solutions, reference should be made to Embodiment 1 or FIGS. 11 to 16, and, regarding the reference numerals, FIG. 25 should be referred to. Regarding the washing solution and the eluting solution, for example, the same solutions used in Embodiment 1 can be used.

Specifically, referring to FIG. 23, following the mixture step, the motor 11 is stopped. The lid of an additional solution ventilation hole 931 is perforated by the perforator 13 to supply air into an additional binding solution container 630. The motor 11 is rotated again, and the reaction solution in the reaction container 820 is pushed out by the additional solution and passed through the nucleic acid binding member. The nucleic acids are adsorbed on the nucleic acid binding member 801, and the solution then flows into a storage container 830.

The motor 11 is then stopped, and the lid of a first washing solution ventilation hole 941 is perforated by the perforator 13 to supply air to a first washing solution container 640. The motor 11 is then rotated again, so that the solution in the first washing solution container flows into the nucleic acid binding member 801, washing unwanted components, such as proteins, that have attached to the nucleic acid binding member 801. Waste liquid after washing flows into a waste liquid storage container 830.

The motor is stopped, and the lid of a second washing solution ventilation hole 941 is perforated by the perforator 13 to supply air to a second washing solution container 650. The lid of a detection container ventilation hole 972 is perforated to communicate a detection container 850 with the outside. Further, the lid of a final washing solution ventilation hole 973 is perforated to communicate a final washing solution disposal container 860 with the outside.

As the motor 11 is rotated again, a second washing solution in the second washing solution container 650 washes the first washing solution that attached to the nucleic acid binding member 801. The second washing solution, after passing through the nucleic acid binding member 801, tends to flow both to the detection container 850 and the waste liquid storage container 830. However, it cannot enter the waste liquid storage container 830 due to the head differences mentioned with regard to the description of Embodiment 1. Instead, the second washing solution flows into the detection container 850, which is referred to as the eluting solution carrier by the invention, while washing the branching portion between the waste liquid storage container and the detection container.

The second washing solution may be ethanol or an aqueous solution of ethanol.

As the amount of the washing solution in the detection container 850 increases, the washing solution overflows out to the final washing solution disposal container 860. All of the solution in the detection container 850 is discharged to the final washing solution disposal container 860 by capillary action and a siphoning effect. However, minute amounts of the solution that have remained on the nucleic acid binding member 801, for example, might flow into the detection container 850 and remain therein after the discharge operation. In such a case, the rotation is stopped once and resumed after an interval, so that the solution remaining in the detection container 850 can be discharged into the final washing solution disposal container 860 by capillary action as well as by a siphoning effect. Thus, with regard to the final washing solution, it is preferable to repeat the process of rotation and stop twice following the perforation of the ventilation holes.

Thereafter, the lid of an eluting solution ventilation hole 961 is perforated by the perforator 13 to supply air into an eluting solution container 660. Further, the lid of an eluting solution disposal ventilation hole 974 is perforated to communicate an eluting solution disposal container 870, which is referred to as the eluting solution disposal portion by the invention, with the outside. The motor 11 is then rotated again, so that the eluting solution flows into the nucleic acid binding member 801. The eluting solution may be water or an aqueous solution with pH adjusted between 7 and 9. It is preferable to heat the eluting solution to temperatures above 40° C. to facilitate elution. The heating may be performed by irradiating the eluting solution container 660 with light from above with the upper optical device 14 shown in FIG. 1.

After passing through the nucleic acid binding member 801, the eluting solution flows into the detection container 850 and further out into the eluting solution disposal container 870. A predetermined quantity of the eluting solution containing nucleic acids is carried in the detection container 850, as in Embodiment 1.

With the motor stopped, the lid of a detection solution ventilation hole 971 is perforated by the perforator 13 to supply air to a detection solution storage container 670. The motor 11 is rotated again, and the detection solution flows to the detection container 850. The detection solution includes deoxynucleoside triphosphate, DNA synthetic enzyme, or fluorescence reagent, for example. Depending on the method of amplification, the detection solution may be heated from above through the detection container 450 by irradiating light with the upper optical device 14.

Next, the lower optical device 15 is transported below the detection container 850 to detect the amount of fluorescence, for example.

The carrier disc 12 must be stopped at predetermined positions during perforation, heating, and detection. As in Embodiment 1, the rotation position of the carrier disc is detected by a position detector 16, as shown in FIGS. 19 and 20, so that the rotation of the motor 11, the rotation and vertical movement of the perforator 13, and the rotation, irradiation, and detection by the upper and lower optical devices 14 and 15 can be controlled by a controller 18.

In accordance with the present embodiment, there is no need to provide a valve in flow passages for controlling the flow of the sample and each reagent. Thus, the problem of the solution remaining at the valve portion in the course of the flow passages does not occur, and the contamination by reagents in pre-process can be prevented. Accordingly, specific components in a liquid sample, such as nucleic acids, can be extracted at high purity and analyzed accurately.

Embodiment 3

While in Embodiments 1 and 2 nucleic acids in a pathogen such as a virus or bacterium and nucleic acids in white blood cells have been extracted from whole blood separately and then analyzed, the individual separation/analysis processes may be performed simultaneously.

Figure 29:
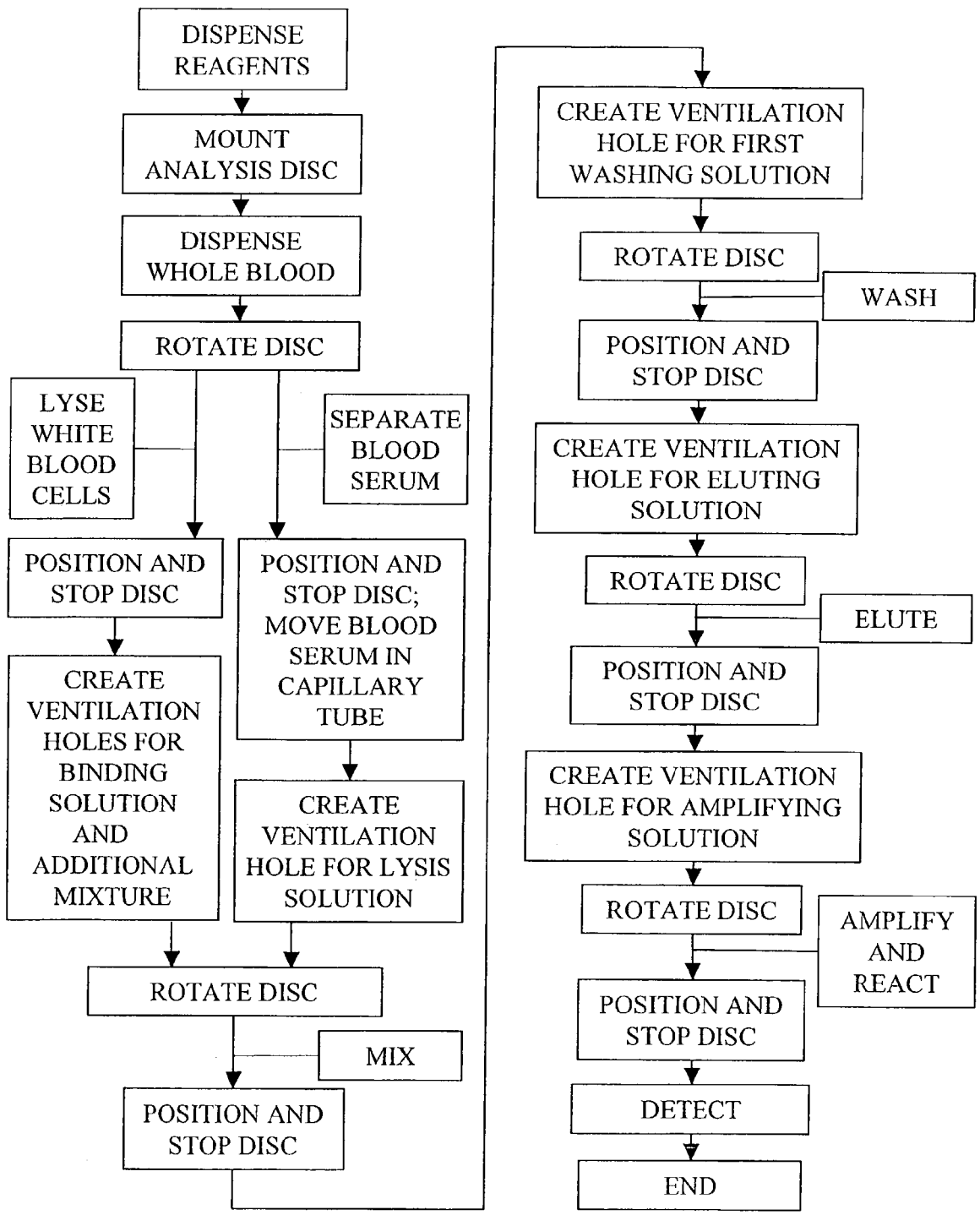
FIG. 29 shows an analysis procedure according to the invention.
Figure 30:
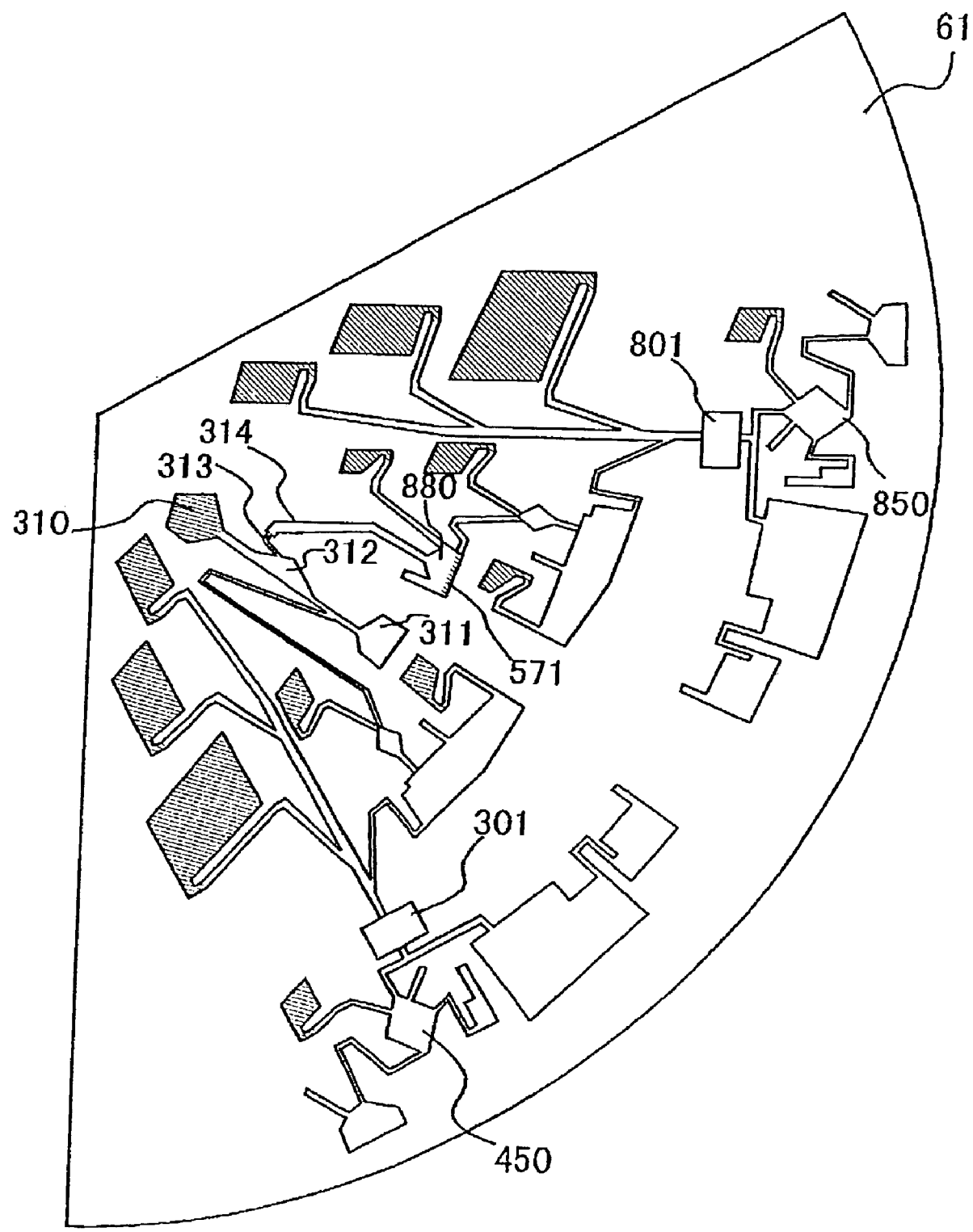
FIG. 30 illustrates the operation of the flow passage portion during the blood serum separation and white blood cell lysis operations according to the invention.
Figure 31:
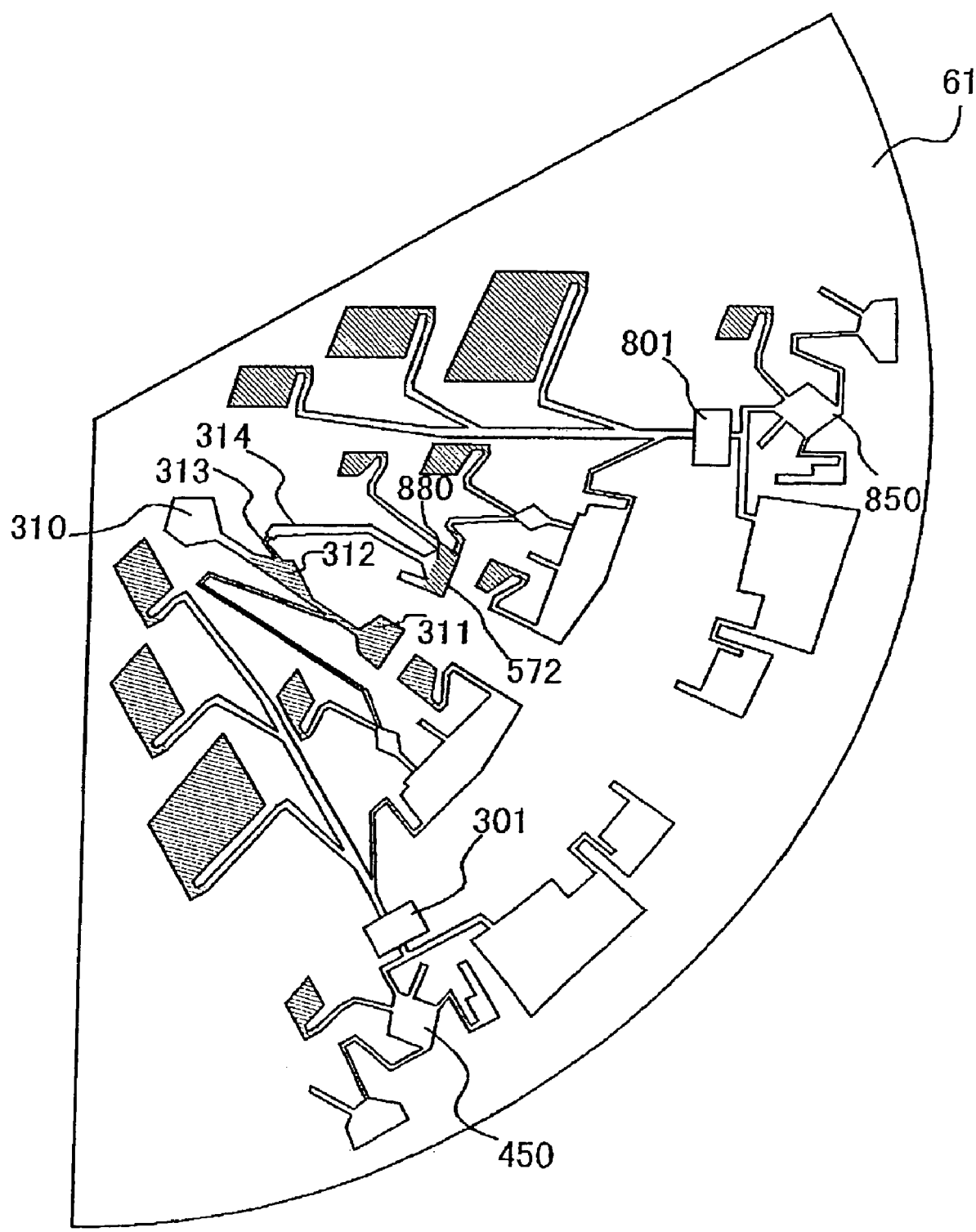
FIG. 31 illustrates the operation of the flow passage portion during the blood serum separation and white blood cell lysis operations according to the invention.

FIG. 29 shows the flow of the extraction/analysis of pathogenic nucleic acids in a virus or bacterium and that of nucleic acids in white blood cells from whole blood that are performed simultaneously. FIGS. 30 and 31 show the flow states during those processes.

As shown in FIG. 30, a flow passage portion 61 comprises flow passages for the extraction/analysis of nucleic acids in a pathogen, as described in Embodiment 1, and flow passages for the extraction/analysis of nucleic acids in white blood cells as described in Embodiment 2, that are formed on a single device.

The extraction/analysis operation consists of the two embodiments performed simultaneously. Specifically, the operator mounts an analysis disc on a carrier disc after injecting the analysis disc with the individual reagents, and then introduces whole blood into a sample container 310 (FIG. 30). As the carrier disc is rotated by the motor, the whole blood introduced into the sample container 310 moves towards the periphery, and fills a blood cell storage container 311 and a blood serum quantitative determination container 312. Excess whole blood flows from a narrow overflow passage 313 via a wide overflow passage 314 to a lysis container 880, and is mixed with a lysis solution 571 in the lysis container 880, thereby lysing the white blood cells in whole blood (FIG. 31).

The subsequent sequence of operations concerning the whole blood in the blood cell storage container 311 and the blood serum quantitative determination container 312 is the same as that in Embodiment 1. Namely, after separation of blood serum, nucleic acids in a pathogen are adsorbed on the nucleic acid binding member 301. The nucleic acids are eluted from the nucleic acid binding member 301 after a plurality of washing steps, and are eventually detected in the detection container 450. Similarly, the operation for the lysis mixture 572 in the lysis container 880 in which whole blood and the lysis solution are mixed is the same as that in Embodiment 2. Specifically, nucleic acids in white blood cells are adsorbed on the nucleic acid binding member 801 and eluted therefrom after a plurality of washing steps. The nucleic acids are eventually detected in the detection container 850.

Thus, in accordance with the present embodiment, nucleic acids in a pathogen and those in white blood cells can be extracted from the same whole blood sample and then analyzed. Accordingly, the presence or absence of infection by a pathogen can be confirmed while at the same time the effect of administering a drug can be predicted based on the patient's genome information so that an optimum drug can be selected. Particularly, the prediction of the drug administration effect only requires the minute amount of whole blood that is produced as a surplus during the extraction of the pathogenic nucleic acids, so that the patient is burdened less when drawing blood.

Embodiment 4

Figure 32:
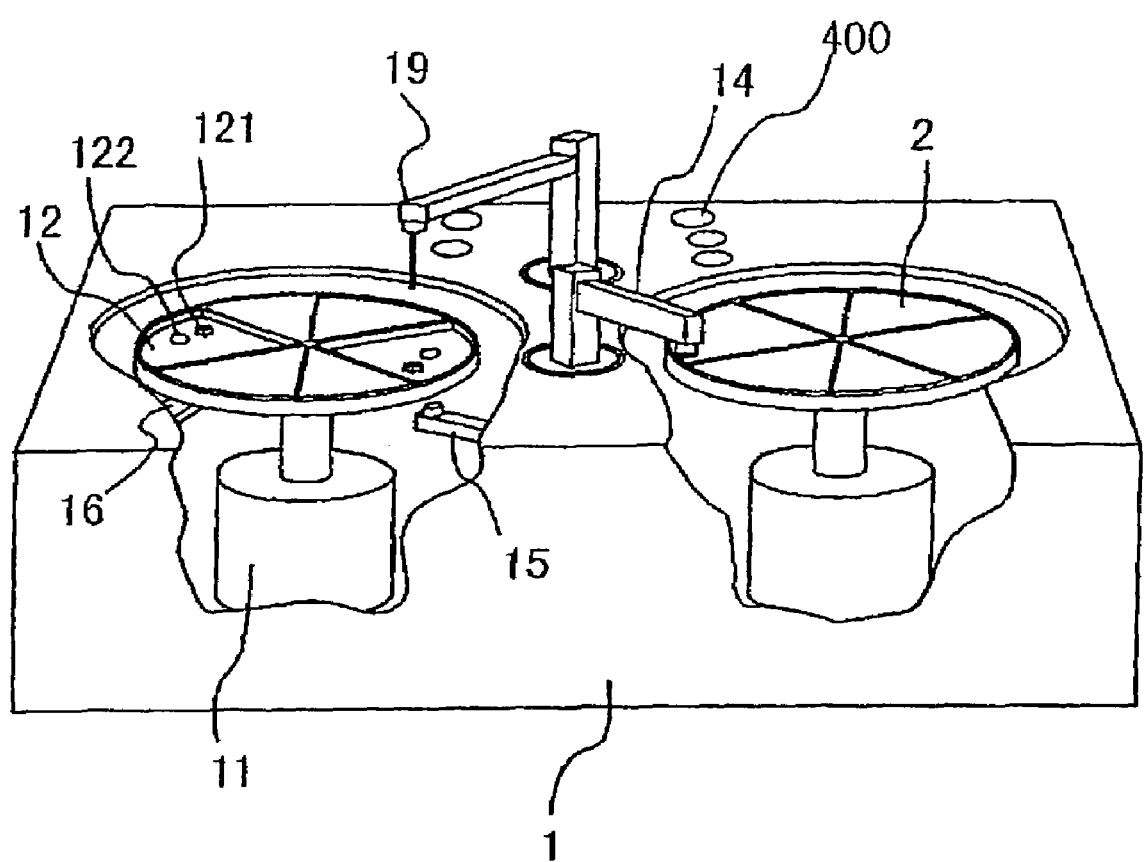
FIG. 32 shows the overall structure of another example of the genetic analysis apparatus according to the invention.
Figure 33:
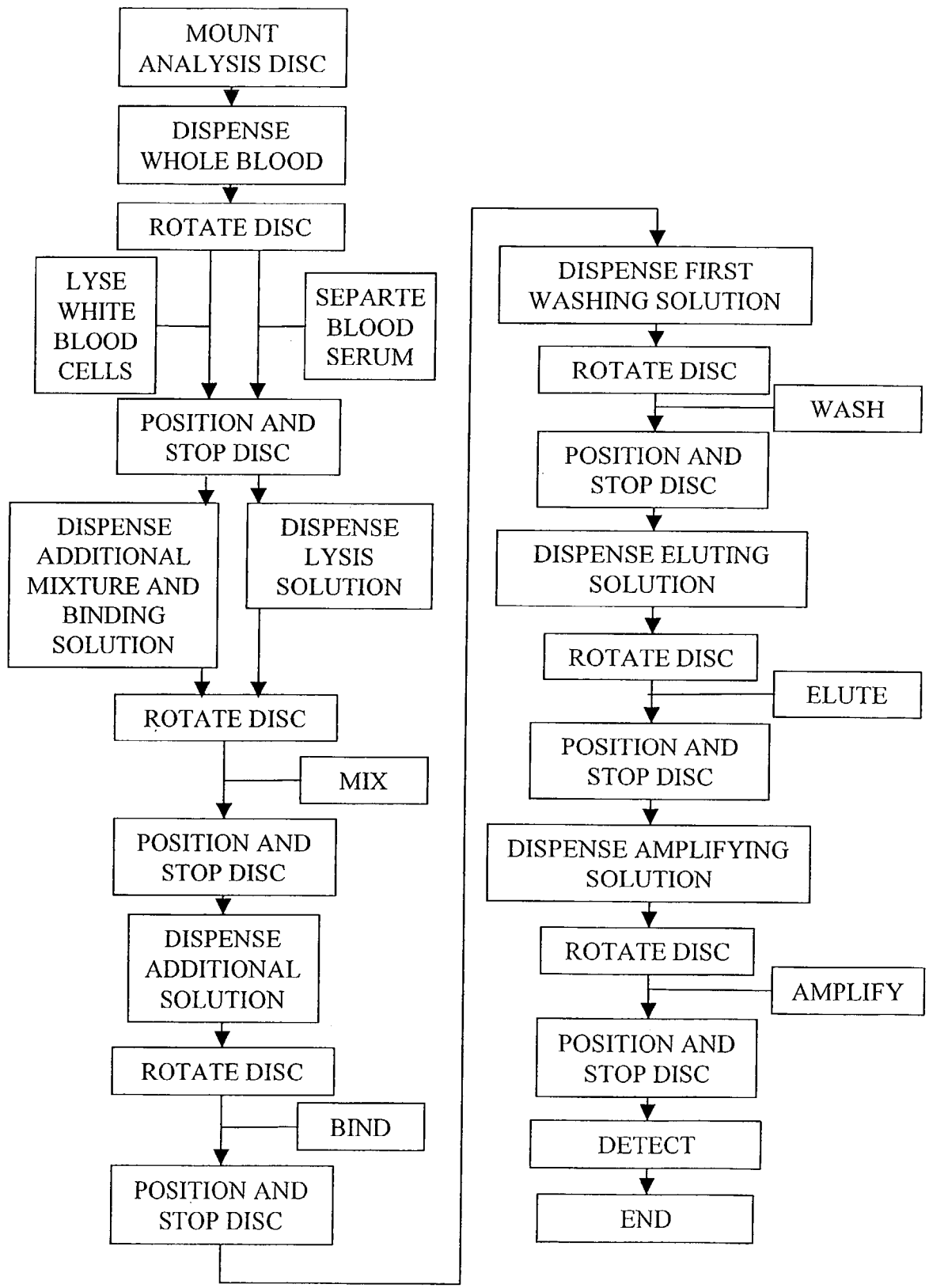
FIG. 33 shows another example of the analysis operation procedure according to the invention.

While in Embodiments 1 to 3 the flow of the reagents was controlled by opening ventilation holes with a perforator, a reagent dispensing mechanism can be used. Specifically, as shown in FIG. 32, after dispensing predetermined reagents from individual reagent bottles 400 into the reagent storage containers shown in FIGS. 6, 25, or 30 with a reagent dispenser 19, the analysis disc is rotated to cause the reagents to flow. The procedure is illustrated in FIG. 33.

In accordance with the present embodiment, there is no need to provide a valve in flow passages for controlling the flow of the sample and each reagent. Thus, the problem of solution remaining at the valve portion in the course of the flow passages does not occur, and the contamination by reagents in the pre-process can be prevented. Accordingly, specific components in a liquid sample, such as nucleic acids, can be extracted with high purity and analyzed accurately.

Furthermore, in accordance with the embodiment, nucleic acids in a pathogen and those in white blood cells can be extracted from the same whole blood sample and then analyzed. Accordingly, the presence or absence of infection by a pathogen can be confirmed while at the same time the effect of administering a drug can be predicted based on the patient's genome information so that an optimum drug can be selected. Particularly, the prediction of the drug administration effect only requires the minute amount of whole blood that is produced as a surplus during the extraction of the pathogenic nucleic acids, so that the patient is burdened less when drawing blood.

What is claimed is:

1. A chemical analysis apparatus comprising a rotatably supported structural member, an optical device for detecting a sample mixed with a reagent in the structural member and a positioning sensor for positioning the structural member, the structural member comprising a captor for capturing a specific chemical substance in a sample, and a plurality of reagent containers for carrying reagents to be flowed to the captor,
wherein the structural member comprises:
a sample supply portion;
a separating portion located more towards the periphery from a rotation center of the structural member than the sample supply portion, wherein the sample component is separated by a difference in specific gravity using centrifugation in the separating portion;
a sample mixing portion where a portion of the sample is mixed with a portion of the reagents;
a pre-separation sample fractionating flow passage for fractionating from the separating portion a pre-separation sample that is a portion of the sample before centrifugation to flow the pre-separation sample to the mixing portion, wherein the pre-separation sample fractioning flow passage connects the separating portion with the sample mixing portion and wherein a connecting portion of the separating portion and the pre-separation sample fractionating flow passage is located more toward the inner periphery of the structural member than a connecting portion of the sample mixing portion and the pre-separation sample fractionating flow passage;
a sample component captor, located more towards the periphery of the structural member than the sample mixing portion, for capturing a chemical substance in the pre-separation sample;
a separated component mixing portion where a portion of the reagents is mixed with a separated component that is a portion of the sample which has been separated by centrifugation;
a separated-component fractionating flow passage for fractionating the separated-component from the separating portion to flow the fractionated separated-component to the separated component to the separated component mixing portion, wherein the separated-component fractionating flow passage connects the separating portion with the separated component mixing portion and wherein a connecting portion of the separating portion and the separated-component fractionating flow passage is located more toward the inner periphery of the structural member than a connecting portion of the sample mixing portion and the separated-component fractionating flow passage and is located more towards the periphery from the rotational center of the structural member than the connecting portion of the separating portion and the pre-separation sample fractionating flow passage; and
a separated component captor, located downstream of the separated component mixing portion, for capturing a chemical substance in the separated component, wherein the separated component captor is located more towards the periphery from the rotational center of the structural member than the separated component mixing portion.

2. The chemical analysis apparatus according to claim 1, wherein the pre-separation sample branching from between the sample supply portion and the separating portion is allowed to flow through a second reagent container carrying a second reagent.

* * * * *